United States Patent
Park et al.

(10) Patent No.: US 10,463,588 B2
(45) Date of Patent: Nov. 5, 2019

(54) COSMETIC COMPOSITION FOR ANTI-AGING OR ALLEVIATING SKIN REDNESS, AND MEDICINAL COMPOSITION FOR PREVENTING AND TREATING SKIN INFLAMMATORY DISEASES, CONTAINING COMPOUND INDUCING INCREASE IN EXPRESSION OF ADIPONECTIN

(71) Applicant: Incospharm Corporation, Daejeon (KR)

(72) Inventors: Kee Don Park, Daejeon (KR); Hwa-Jee Chung, Daejeon (KR); Heung Jae Kim, Daejeon (KR); Chae Jin Lim, Daejeon (KR); Seok Jeong Yoon, Daejeon (KR); Jong Phill Kang, Daejeon (KR); Seon Deok Kwon, Daejeon (KR); Myung Ho Kor, Daejeon (KR); Ju Yeon Jung, Sejong-si (KR); Beom Cheol Kim, Daejeon (KR); Ka Young Shin, Daejeon (KR)

(73) Assignee: Incospharm Corporation, Daejeon (KR)

( * ) Notice: Subject to any disclaimer, the term of this patent is extended or adjusted under 35 U.S.C. 154(b) by 0 days.

(21) Appl. No.: 15/958,936

(22) Filed: Apr. 20, 2018

(65) Prior Publication Data

US 2018/0303733 A1   Oct. 25, 2018

(30) Foreign Application Priority Data

Apr. 20, 2017 (KR) .......................... 10-2017-0050831
Apr. 18, 2018 (KR) .......................... 10-2018-0045029

(51) Int. Cl.
*A61K 8/44* (2006.01)
*A61K 8/06* (2006.01)
*A61K 8/04* (2006.01)
*A61K 8/02* (2006.01)
*A61Q 19/02* (2006.01)
*A61Q 19/08* (2006.01)
*A61K 31/198* (2006.01)

(52) U.S. Cl.
CPC ................ *A61K 8/44* (2013.01); *A61K 8/022* (2013.01); *A61K 8/042* (2013.01); *A61K 8/044* (2013.01); *A61K 8/06* (2013.01); *A61K 31/198* (2013.01); *A61Q 19/02* (2013.01); *A61Q 19/08* (2013.01); *A61K 2800/43* (2013.01); *A61K 2800/48* (2013.01); *A61K 2800/522* (2013.01); *A61K 2800/524* (2013.01)

(58) Field of Classification Search
None
See application file for complete search history.

(56) References Cited

PUBLICATIONS

Chen et al., "The Roles of Autophagy and the Inflammasome during Environmental Stress-Triggered Skin Inflammation", International Journal of Molecular Sciences, vol. 17, No. 12—16 pages, (Dec. 9, 2016).

Fang et al., "Dermal Lipogenesis Inhibits Adiponectin Production in Human Dermal Fibroblasts while Exogenous Adiponectin Administration Prevents against UVA-Induced Dermal Matrix Degradation in Human Skin", International Journal of Molecular Sciences, vol. 17, No. 7—17 pages, (Jul. 14, 2016).

Fisher et al., "Pathophysiology of Premature Skin Aging Induced by Ultraviolet Light", The New England Journal of Medicine, vol. 337, No. 20—10 pages, (Nov. 13, 1997).

Kim et al., "UV-induced inhibition of adipokine production in subcutaneous fat aggravates dermal matrix degradation in human skin", Scientific Reports, vol. 6—10 pages, (May 10, 2016).

*Primary Examiner* — Jeffrey S Lundgren
*Assistant Examiner* — Stephanie K Springer
(74) *Attorney, Agent, or Firm* — Knobbe Martens Olson & Bear LLP

(57) ABSTRACT

Provided are a cosmetic composition for anti-aging or alleviating skin redness, and a medicinal composition for treating and preventing skin inflammatory diseases caused by light, containing a compound inducing an increase in expression of adiponectin or a pharmaceutically acceptable salt thereof.

5 Claims, 7 Drawing Sheets

[FIG. 1]
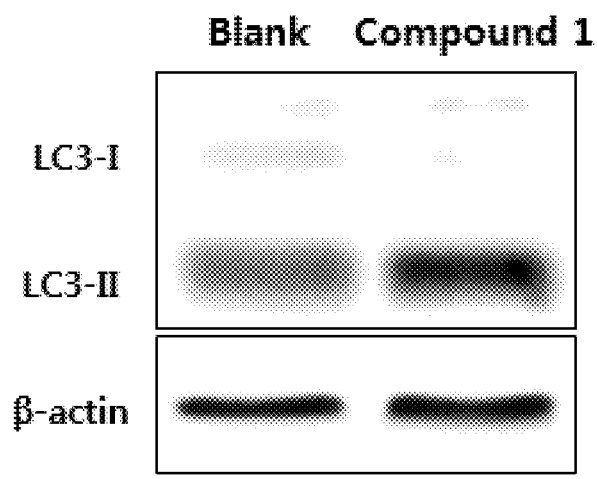
[FIG. 2]
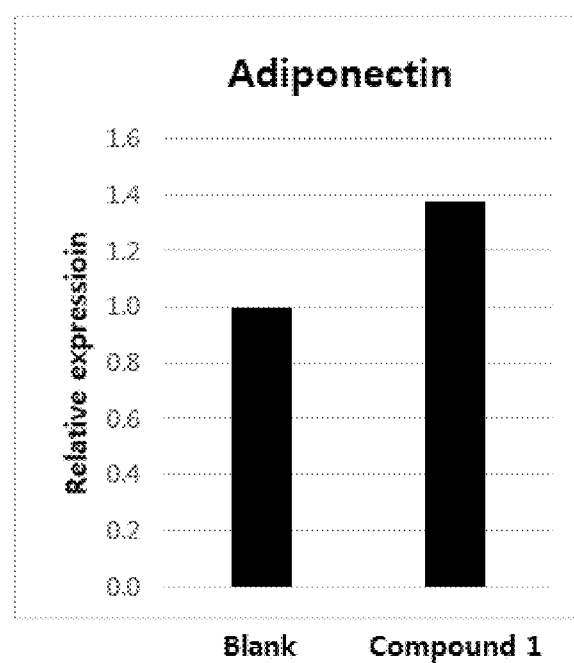

[FIG. 3]
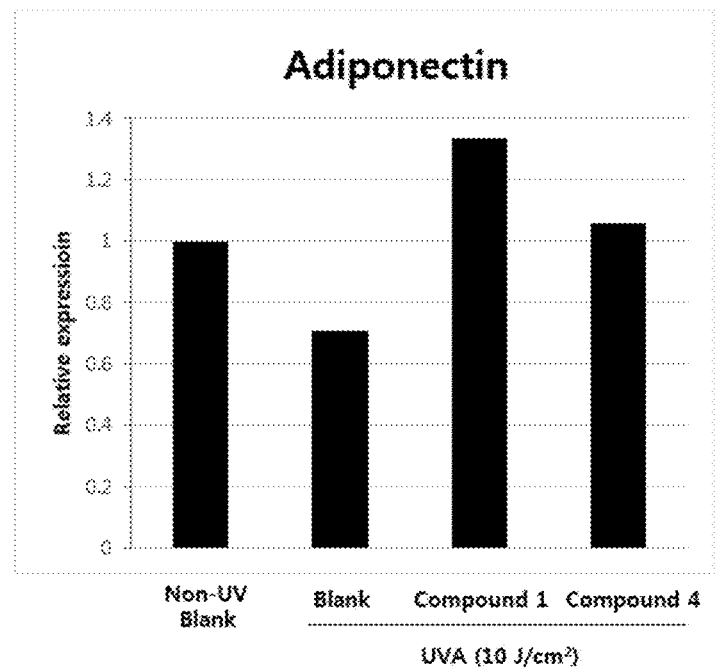
[FIG. 4]
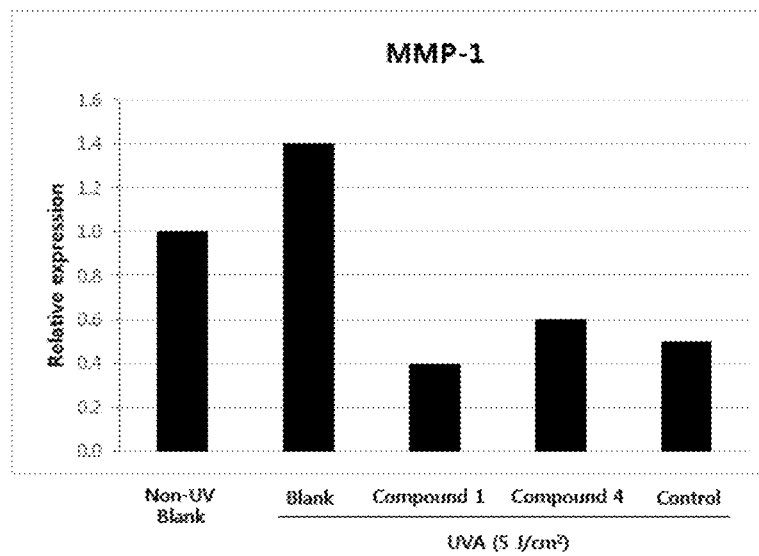

[FIG. 5]
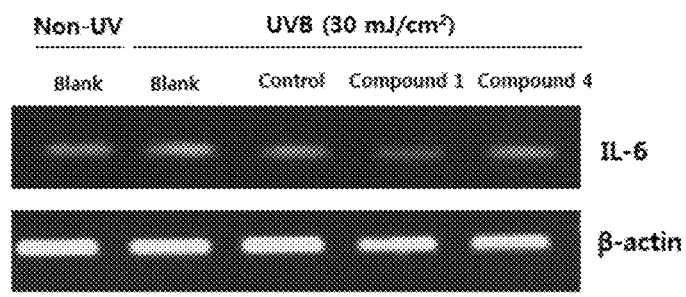
[FIG. 6]
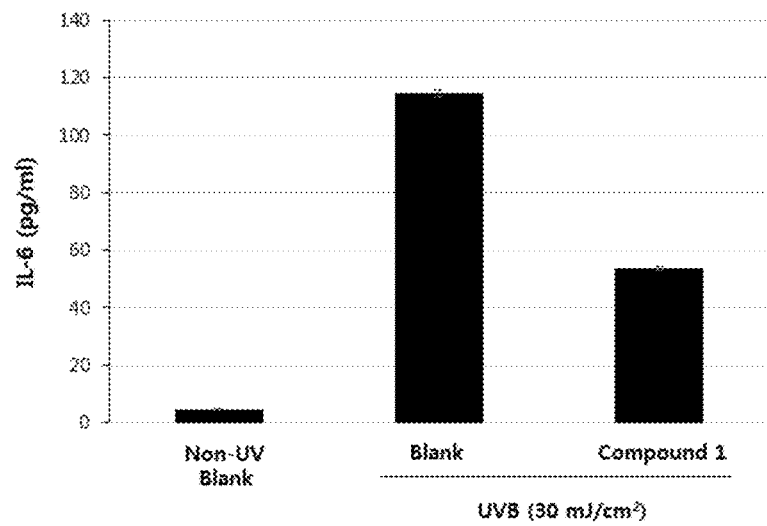

[FIG. 7]
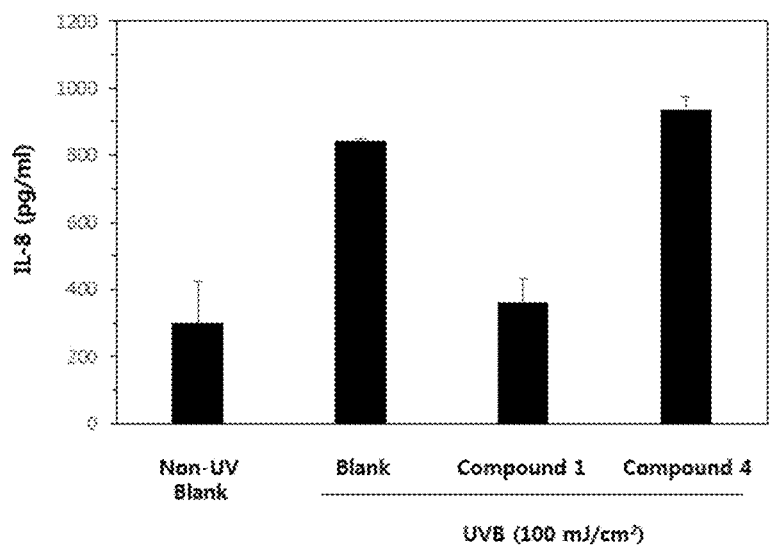
[FIG. 8]
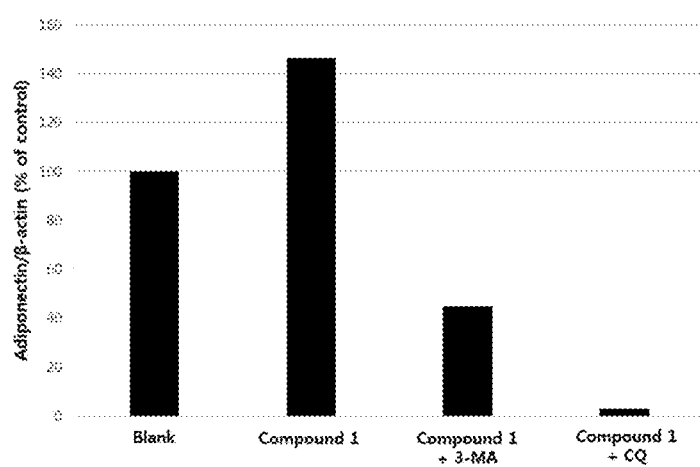

[FIG. 9]
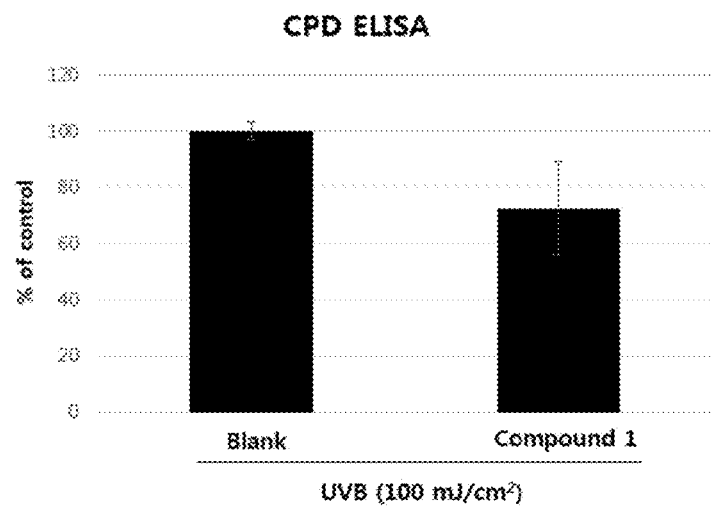
[FIG. 10]
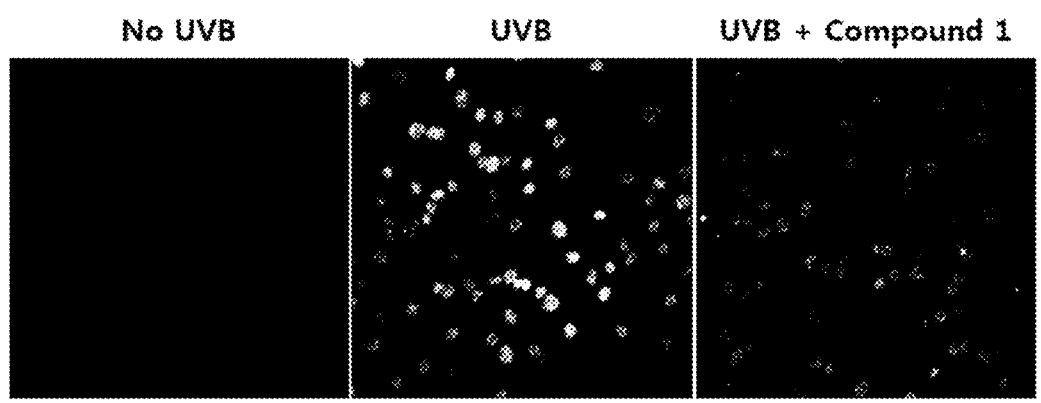

[FIG. 11]
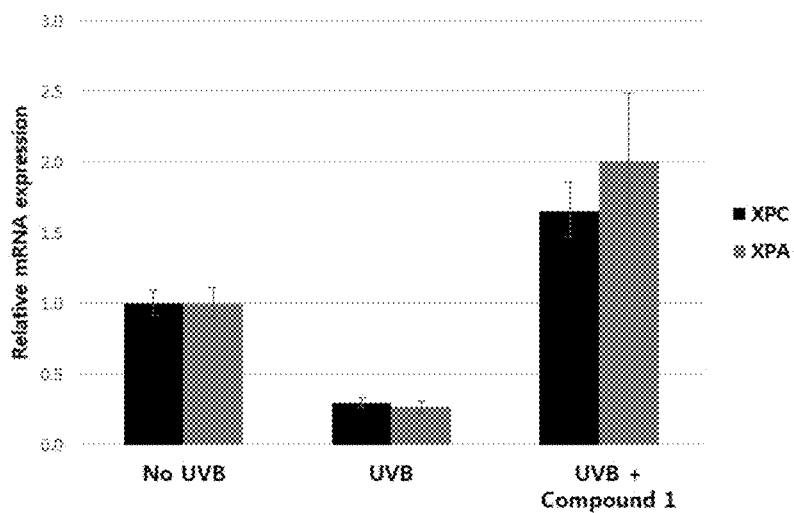
[FIG. 12]
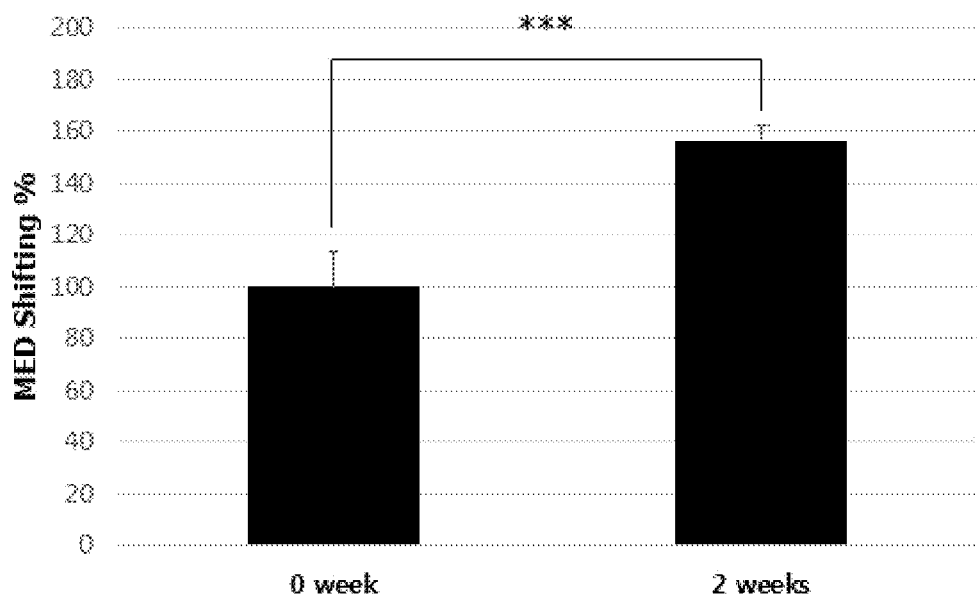
***p<0.001

[FIG. 13]
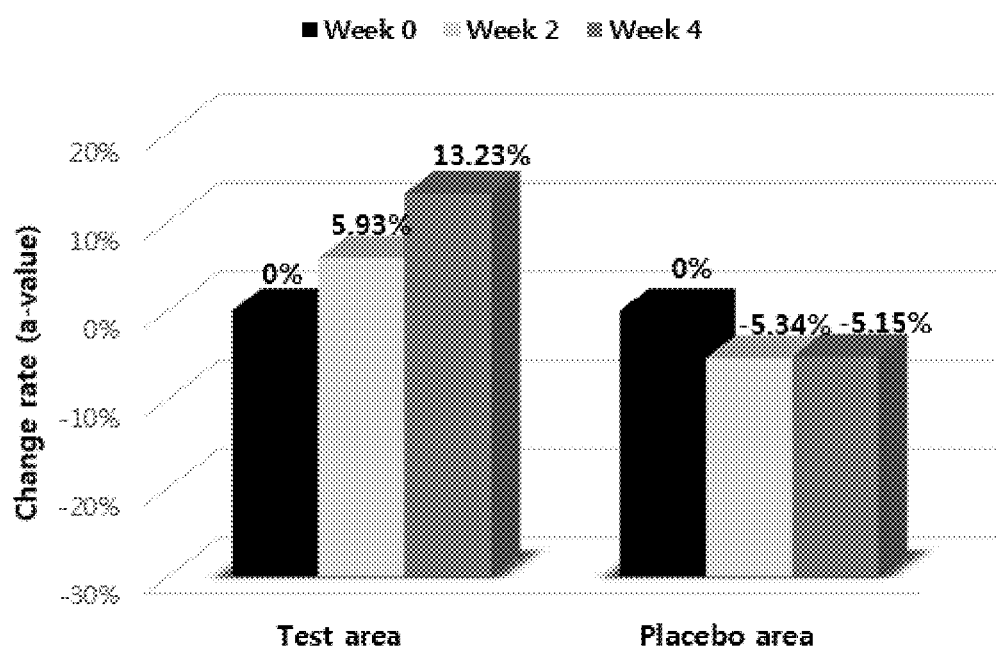

COSMETIC COMPOSITION FOR ANTI-AGING OR ALLEVIATING SKIN REDNESS, AND MEDICINAL COMPOSITION FOR PREVENTING AND TREATING SKIN INFLAMMATORY DISEASES, CONTAINING COMPOUND INDUCING INCREASE IN EXPRESSION OF ADIPONECTIN

CROSS-REFERENCE TO RELATED APPLICATIONS

This application claims priority under 35 U.S.C. § 119 to Korean Patent Application No. 10-2017-0050831, filed on Apr. 20, 2017 and Korean Patent Application No. 10-2018-0045029, filed on Apr. 18, 2018, in the Korean Intellectual Property Office, the disclosure of which is incorporated herein by reference in its entirety.

TECHNICAL FIELD

The following disclosure relates to a cosmetic composition for anti-aging or alleviating skin redness and a medicinal composition for preventing and treating skin diseases, and more particularly, to a cosmetic composition for anti-aging or alleviating skin redness, and a medicinal composition for preventing and treating skin inflammatory diseases, containing a compound inducing an increase in expression of adiponectin and an autophagy activity or a pharmaceutically acceptable salt thereof.

BACKGROUND

Repetition of skin damage and regeneration due to ultraviolet (UV) light of sun light forms wrinkles, which leads to "photo-aging". Chronic exposure to UV light increases expression of matrix metalloproteinases (MMPs) and destroys collagen corresponding to an extracellular matrix (ECM) protein which is important in elasticity and strength of the skin tissue while occupying 80% or more of the dermis layer. The destroyed collagen is accumulated in a deformed form during the process of wound healing, resulting in the formation of clinical wrinkles. Further, continuous exposure of the skin to UV light increases secretion of inflammatory cytokines, thereby causing chronic skin inflammatory response.

Meanwhile, adiponectin, a representative adipokine secreted in adipocytes, is known to have functions of as lipogenesis and lipolysis, regulation of the appetite, insulin resistance, and inflammation, etc. Recently, researches have shown that adiponectin is decreased in the subcutaneous adipocytes of the photo-aged skin. It has been reported that decreasing expression of adiponectin by UV light accelerates photo-aging by increasing MMP-1 and inhibiting collagen biosynthesis.

Further, autophagy is a mechanism to regenerate energy and remove damaged materials by degradingaged or damaged intracellular materials and organelles in cells when an energy source in the cells is exhausted or stress factors in cells are excessively generated, and autophagy enables maintenance of normal cells. In addition to maintain intracellular homeostasis, autophagy is also involved in immune cell responses and inflammatory pathway. Mechanism for removing microorganisms in cells is provided through autophagy acceptors.

Recently, in various studies, it was reported that as the aging has proceeded or been accelerated, the autophagy activity in cells has rapidly decreased. Further, in the case of suppressing the autophagy, aged mitochondria, misfolded proteins, or the like, are excessively accumulated in cells, such that free radicals and oxidative stress in the cells are increased, thereby resulting in increasing apoptosis and promoting aging. Therefore, denatured proteins, lipid, mitochondria, and the like, may be rapidly removed by activating autophagy mechanism to decompose aged materials and organelles in cells and reuse decomposed products, such that an environment in which cells may live in a healthier state may be provided.

Therefore, it is expected that in the case of developing a novel active material capable of promoting autophagy activation in cells while increasing expression of adiponectin, the damaged skin of wrinkles due to UV light, toxic substances caused by oxidative stress and micro inflammatory environment will be recovered, thereby preventing photoaging.

The disclosure of this section is to provide background of the invention. Applicant notes that this section may contain information available before this application. However, by providing this section, Applicant does not admit that any information contained in this section constitutes prior art.

RELATED ART DOCUMENT

Non-Patent Document

The New England Journal of Medicine, 1997; 337:1419-29

Scientific Reports, 2016; 6: 25616-25

International Journal of Molecular Sciences, 2016, 17(7), 1129-1145

International Journal of Molecular Sciences, 2016, 17(12): 2063-2078

SUMMARY

An embodiment of the present invention is directed to providing a cosmetic composition for anti-aging, containing a compound capable of inducing an increase in expression of adiponectin and autophagy activation or a pharmaceutically acceptable salt thereof, particularly, a cosmetic composition for anti-aging capable of preventing skin inflammatory diseases due to photo-aging or alleviating wrinkles due to UV light and inflammation.

Another embodiment of the present invention is directed to providing a cosmetic composition for alleviating skin redness containing a compound capable of inducing an increase in expression of adiponectin and autophagy activation or a pharmaceutically acceptable salt thereof.

Another embodiment of the present invention is directed to providing a medicinal composition for preventing and treating skin inflammatory diseases caused by light, containing a compound inducing an increase in expression of adiponectin and autophagy activation or a pharmaceutically acceptable salt thereof.

In one general aspect, a cosmetic composition for anti-aging contains a compound represented by the following Chemical Formula 1 or a pharmaceutically acceptable salt thereof, the compound serving to suppress formation of wrinkles and inflammation by UV light of sun light and decrease oxidative stress by increasing expression of adiponectin and an autophagy activity.

[Chemical Formula 1]

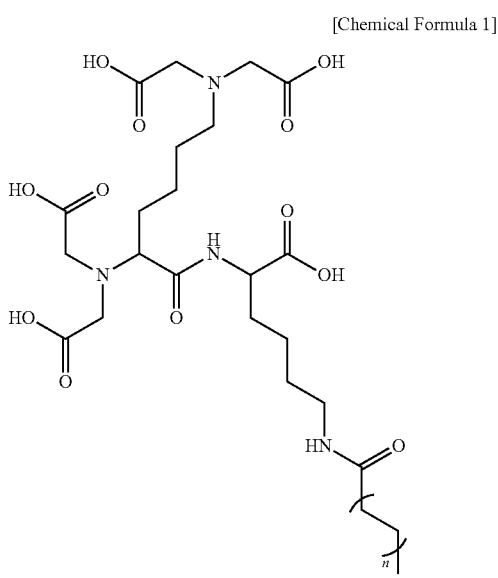

(In Chemical Formula 1,
n is an integer of 2.)

In another general aspect, a cosmetic composition for alleviating skin redness contains a compound represented by Chemical Formula 1 or a pharmaceutically acceptable salt thereof, the compound serving to decrease skin redness by UV light of sun light by increasing expression of adiponectin and an autophagy activity.

Preferably, the compound represented by Chemical Formula 1 according to an embodiment of the present invention may be represented by Chemical Formula 2 in view of more excellent anti-aging and skin redness alleviation effects.

[Chemical Formula 2]

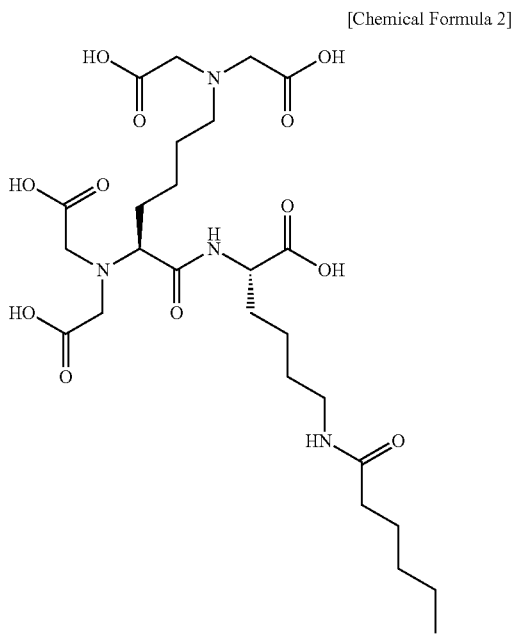 [SMILES: CCCCCC(=O)NCCCC[C@H](NC(=O)[C@H](CCCCN(CC(=O)O)CC(=O)O)N(CC(=O)O)CC(=O)O)C(=O)O]

Preferably, in the cosmetic composition according to the embodiment of the present invention, the compound inducing an increase in expression of adiponectin, represented by Chemical Formula 1 or the pharmaceutically acceptable salt thereof may be contained in a content of 0.0001 to 10 wt %, and the cosmetic composition may be formulated into formulations such as suspensions, emulsions, pastes, gels, creams, lotions, powders, soaps, surfactant-containing cleansing formulations, oils, powder foundations, emulsion foundations, wax foundations, or sprays.

Preferably, the cosmetic composition according to the embodiment of the present invention may be to prevent and treat wrinkles, redness, or skin aging due to photo-aging.

In another general aspect, a medicinal composition for preventing and treating skin inflammatory diseases caused by light, contains a compound inducing an increase in expression of adiponectin, represented by Chemical Formula 1 according to embodiments of the present invention.

In the medicinal composition according to the embodiment, the compound inducing an increase in expression of adiponectin or a pharmaceutically acceptable salt thereof may be contained in a content of 0.0001 to 10 wt %.

BRIEF DESCRIPTION OF THE DRAWINGS

FIG. 1 is a result obtained by analyzing expression of protein associated with autophagy activation by treatment of a compound 1 according to embodiments of the present invention.

FIG. 2 is a result obtained by analyzing gene expression of adiponectin by the compound 1 according to embodiments of the present invention.

FIG. 3 is a result obtained by comparing and analyzing gene expression of UV-induced adiponectin by compounds 1 and 4 according to embodiments of the present invention.

FIG. 4 is a result obtained by analyzing gene expression of UV-induced MMP-1 by the compounds 1 and 4 according to embodiments of the present invention.

FIG. 5 is a result obtained by analyzing gene expression of UV-induced inflammatory cytokine, interleukin-6 (IL-6) by the compounds 1 and 4 according to embodiments of the present invention.

FIG. 6 is a result obtained by analyzing a change in secretion of UV-induced inflammatory cytokine, interleukin-6 (IL-6) by the compound 1 according to embodiments of the present invention.

FIG. 7 is a result obtained by analyzing a change in secretion of UV-induced inflammatory cytokine, interleukin-8 (IL-8) by the compounds 1 and 4 according to embodiments of the present invention.

FIG. 8 is a result illustrating an increase in formation of adiponectin due to an autophagy activity of the compound 1 according to embodiments of the present invention.

FIG. 9 is an enzyme-linked immunosorbent assay (ELISA) analysis result for a change in formation of cyclobutane pyrimidine dimer (CPD), which is a UV-induced DNA damage product, by the compound 1 according to embodiments of the present invention.

FIG. 10 is a result obtained by observing a change in formation of CPD, which is a UV-induced DNA damage product, by the compound 1 according to embodiments of the present invention through an intensity of green fluorescence.

FIG. 11 is a result obtained by analyzing xeroderma pigmentosum, complementation groups A and C (XPC and XPA) gene expression with respect to repair of UV-damaged DNA by the compound 1 according to embodiments of the present invention.

FIG. 12 is a result obtained by measuring an increase rate of a minimal erythema dose (MED) as a result of an efficacy test of the compound 1 according to embodiments of the present invention in prevention of UV damage in a human body.

FIG. 13 is results illustrating degrees of alleviation of skin redness in a test site and a control site, expressed as percentages as results of an efficacy test of the compound 1 according to embodiments of the present invention in alleviation of skin redness.

DETAILED DESCRIPTION OF EMBODIMENTS

Embodiments of the present invention provides a cosmetic composition for anti-aging or alleviating skin redness capable of preventing and improving skin aging caused by various factors by containing a compound inducing an increase in expression of adiponectin to increase expression of adiponectin and proteins associated with autophagy activation or a pharmaceutically acceptable salt thereof, wherein the compound inducing an increase in expression of adiponectin according to embodiments of the present invention is represented by the following Chemical Formula 1.

a compound corresponding to a case in which n is 2, increases expression of adiponectin while inducing autophagy activation to have an anti-aging effect and decrease skin redness, preferably, decrease decomposition of collage proteins by UV light of sun light, thereby having surprising effects against photo-aging, skin redness, oxidative stress, and the like.

The compound inducing an increase in expression of adiponectin, represented by Chemical Formula 1 according to embodiments of the present invention contains one or more chiral asymmetric carbon atoms, such that the compound inducing an increase in expression of adiponectin, represented by Chemical Formula 1 may be present in a racemic form and optically active form. All the compounds as described above and the enantiomers thereof are included in the scope of the present invention.

Preferably, the compound represented by Chemical Formula 1 according to the embodiment of the present invention may be represented by Chemical Formula 2 in view of excellent anti-aging and skin redness alleviation effects.

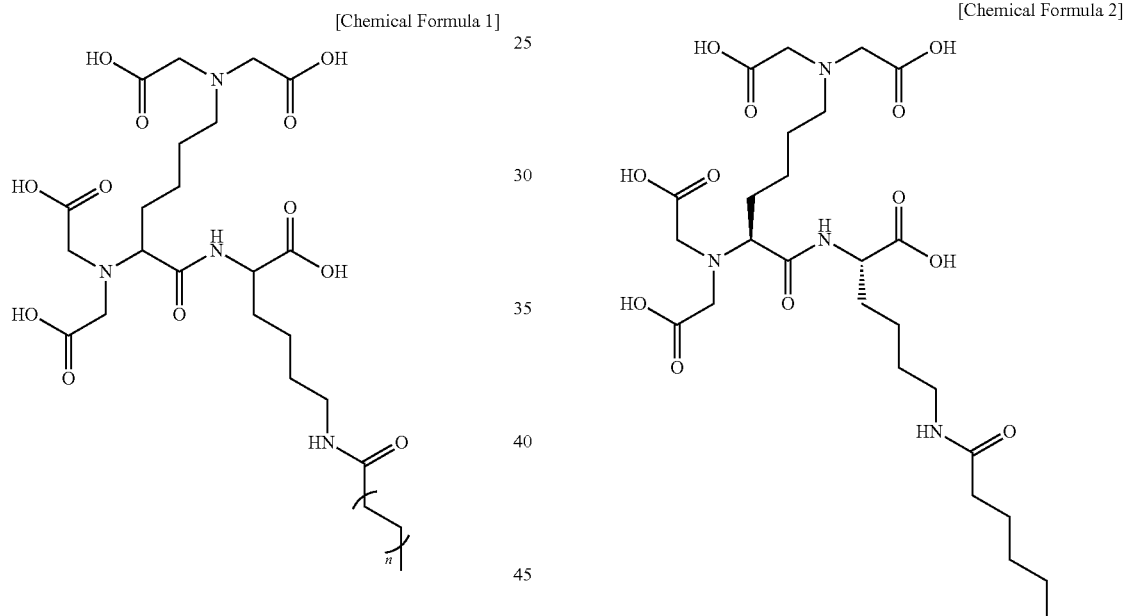

[Chemical Formula 1]

[Chemical Formula 2]

(In Chemical Formula 1,
n is an integer of 2.)

The compound represented by Chemical Formula 1, contained in the cosmetic composition for anti-aging and alleviating skin redness according to embodiments of the present invention is a compound significantly effective in anti-aging or skin redness alleviation. Surprisingly, in compounds corresponding to cases in which only n is 0, 1, and 3 to 10 in Chemical Formula 1, an anti-aging effect of the compound represented by Chemical Formula 1 according to embodiments of the present invention is not exhibited.

In other words, surprisingly, in each of the compounds corresponding to the cases in which n is 0, 1, and 3 to 10, which has the same back bone as that of the compound according to embodiments of the present invention and is different from the compound according to embodiments of the present invention in view of the number of alkyls, only autophagy activation was induced, but expression of adiponectin was not increased.

Only the compound represented by Chemical Formula 1 according to embodiments of the present invention, that is, In tissue and cells of young people, autophagy activation in cells actively occurs, but as an aging process proceeds, since expression amounts of proteins associated with autophagy in cells are rapidly decreased, autophagy activity is rapidly decreased, such that aged proteins, lipids, and mitochondria in the cells are not timely removed and thus, a cell aging phenomenon rapidly occurs.

Therefore, the compound represented by Chemical Formula 1 according to embodiments of the present invention may activate autophagy in cells, thereby making it possible to suppress aging of each cell, tissue, and individual, alleviate skin redness, and prevent and treat skin diseases caused by aging.

Further, the present inventors found that the compound inducing an increase in expression of adiponectin according to embodiments of the present invention may activate expression of adiponectin of which formation is decreased at the time of exposure to light while activating autophagy, thereby completing embodiments of the present invention.

As a result, the compound inducing an increase in expression of adiponectin represented by Chemical Formula 1 according to embodiments of the present invention or the pharmaceutically acceptable salt thereof is significantly effective in anti-aging of the skin or alleviating skin redness by increasing expression of adiponectin decreased by light while increasing expression of the protein associated with autophagy activation, such that the compound inducing an increase in expression of adiponectin or the pharmaceutically acceptable salt thereof may be significantly usefully used to prevent, improve, or treat skin diseases, particularly, inflammatory diseases, caused by light.

The cosmetic composition for anti-aging and alleviating skin redness according to embodiments of the present invention has excellent storage stability and is useful for improving or preventing skin-aging caused by various causes, preferably, light, and more preferably, UV light. Further, the cosmetic composition is more useful for improving and preventing photo-aging or oxidative stress. More specifically, the cosmetic composition is useful for preventing or improving wrinkles or skin aging.

As used herein, the term "wrinkles" means fine lines formed by skin degeneration, and the wrinkles may be caused by a genetic cause, a decrease in collagen present in the skin dermis, an external environment, and the like.

As used herein, the term "skin aging" means appearance of symptoms such as a decrease in elasticity of the skin, a decrease in gross, formation of wrinkles, weakening of regeneration power, severe dryness, or the like, and the "skin aging" may be caused by the passage of time, external environments, or the like.

As used herein, the term "skin redness" means a phenomenon that redness of the skin is increased, and the skin redness may be caused by environmental factors such as UV light, air pollution, and climate, intrinsic factors such as acne, psoriasis, changes in hormones, and the like. In the cosmetic composition for anti-aging and alleviating skin redness according to embodiments of the present invention, a content of the compound inducing an increase in expression of adiponectin represented by Chemical Formula 1 may be suitably adjusted depending on uses, application formulations, purposes of use, and the desired effect of the composition. For example, considering effects as compared to the content, the content of the compound inducing an increase in expression of adiponectin is 0.0001 to 10 wt %, preferably 0.001 to 5 wt %, more preferably, 0.001 to 1 wt %, and most preferably 0.03 to 0.1 wt % based on a weight of the entire composition. When the content is less than the above-mentioned range, it is impossible to substantially obtain the effect of activating autophagy and increasing expression of adiponectin, and when the content is more than the above-mentioned range, stability and a storage property of a formulation may be deteriorated. Therefore, it is preferable that the content of the compound inducing an increase in expression of adiponectin is within the above-mentioned range.

The cosmetic composition for anti-aging and alleviating skin redness according to embodiments of the present invention may additionally contain all kinds of ingredients capable of being generally used for production or formulation, for example, a perfume, a colorant, a disinfectant, an anti-oxidant, a preservative, a moisturizer, a stabilizer, an emulsifier, a thickener, a liquid crystal membrane reinforcing agent, a pigment, an excipient, a diluent, inorganic salts, a synthetic polymer material, and the like, in addition to the compound inducing an increase in expression of adiponectin represented by Chemical Formula 1 according to embodiments of the present invention or the pharmaceutically acceptable salt thereof, and the kinds and contents thereof may be suitably adjusted depending on uses and purposes of use of a final product.

The additives capable of being additionally contained are not limited as long as they are generally used in the art. As a specific example, a preservative such as propanediol, 1,2-hexanediol, ethylhexyl glycerin, phenoxyethanol, caprylhydroxamic acid, or glyceryl caprylate; a UV absorber such as methoxycinnamic acid derivatives, diphenyl acrylic acid derivatives, salicylic acid derivatives, para-aminobenzoic acid derivatives, triazine derivatives, benzophenon derivatives, benzal malonate derivatives, anthranyl derivatives, imidazoline derivatives, 4,4-diarylbutadiene derivatives, or phenyl benzimidazole derivatives; a stabilizer selected from fatty alcohols such as stearyl alcohol, cetyl alcohol, and behenyl alcohol and silicon polymers such as bis-PEG 15/methyl ethyl dimethyl silane, dimethicone/dimethicone PEG-10/15, dimethicone/polyglycerine-3, dimethicone/dimethiconol, dimethicone/dimethicone vinyldimethicone, cyclomethicone/dimethiconol, cyclomethicone/dimethicone, cyclomethicone/trimethylsiloxysilicate, cyclopentasiloxane/dimethicone, cyclopentasiloxane/PEG-12 dimethicone, cyclopentasiloxane/cetearyl dimethicone/vinyl dimethicone, and cyclopentasiloxane/dimethicone/vinyl dimethicone, a dimethicone/vinyl dimethicone crosspolymer; and an emulsifier selected from cationic surfactants, anionic surfactants, amphiphilic surfactants, non-ionic surfactants, and the like, may be mixed. Preferably, as a polyglyceryl fatty acid ester based surfactant such as polyglyceryl-4 caprylate/caprate, polyglyceryl-5 caprylate/caprate, polyglyceryl-6 caprylate/caprate, polyglyceryl-7 caprylate/caprate, polyglyceryl-8 caprylate/caprate, polyglyceryl-9 caprylate/caprate, polyglyceryl-10 caprylate/caprate, polyglyceryl-4 caprate, polyglyceryl-5 caprate, polyglyceryl-6 caprate, polyglyceryl-7 caprate, polyglyceryl-8 caprate, polyglyceryl-9 caprate, polyglyceryl-10 caprate, polyglyceryl-4 laurate, polyglyceryl-5 laurate, polyglyceryl-6 laurate, polyglyceryl-7 laurate, polyglyceryl-8 laurate, polyglyceryl-9 laurate, polyglyceryl-10 laurate, polyglyceryl-6 cocoate, polyglyceryl-7 cocoate, polyglyceryl-8 cocoate, polyglyceryl-9 cocoate, polyglyceryl-10 cocoate, polyglyceryl-11 cocoate, polyglyceryl-12 cocoate, polyglyceryl-6 myristate, polyglyceryl-7 myristate, polyglyceryl-8 myristate, polyglyceryl-9 myristate, polyglyceryl-10 myristate, polyglyceryl-11 myristate, polyglyceryl-12 myristate, polyglyceryl-10 oleate, polyglyceryl-oleate, polyglyceryl-12 oleate, polyglyceryl-10 stearate, polyglyceryl-11 stearate, polyglyceryl-12 stearate, or polyglyceryl-6 behenate, a surfactant directly prepared by reacting polyglyceryl and fatty acid with each other or a commercially available surfactant may be used. The thickener, which is to impart a suitable viscosity to the cosmetic composition to improve feeling of use and stability of the formulation, may be selected from carbomer, carbopol, gelatin, xanthan gum, natural cellulose, hycell, methyl cellulose, and the like, but is not limited thereto. The liquid crystal membrane reinforcing agent, which serve to increase strength of a liquid crystal and tightly connect fences to maintain long-term stability of the liquid crystal, may be phytosphingosine, bishydroxyethyl biscetyl malonamide, cholesterol isostearate, cholesterol oleate, cholesterol stearate, lecithin, ceramides, (for example, ceramide 3, ceramide 6), or the like, but is not limited thereto.

Further, examples of the pigment include extender pigments, white pigments, coloring pigments, nacreous pigments, metal powders, organic powders, and the like.

Examples of the extender pigment may include talc, mica, kaolin, calcium carbonate, alumina, barium silicate, zeolite, muscovite, magnesium carbonate, barium sulfate and the like, examples of the white pigment may include titanium oxide, zinc oxide, and the like, examples of the coloring pigment may include bengala, yellow iron oxide, black iron oxide, chromium oxide, ultramarine, iron blue, carbon black, and the like, examples of the nacreous pigment may include titanium dioxide, titanated mica, iron titanate, titanium oxide coated mica, silica, tin oxide, ferric ferrocyanide, and the like, examples of the metal powder may include gold powder, silver powder, copper powder, palladium powder, platinum powder, and the like, and examples of the organic powder may include polymethylmethacrylate, nylon, cellulose, starch, and the like. Further, all of the natural, inorganic and organic pigments generally known in the cosmetic art may be used. As the natural pigment, one selected from the group consisting of gardenia yellow, gardenia blue, gardenia green, gardenia red, a monascus red colorant, a monascus yellow colorant, a carthamus yellow colorant, an annatto colorant, a cochineal colorant, a lac colorant, a kaoliang colorant, a graph skin colorant, a red cabbage colorant, an elderberry colorant, a blueberry colorant, a paprika colorant, a caramel colorant, a red radish colorant, a persimmon colorant, riboflavin, beta-carotene, a cacao colorant, a turmeric colorant, a corn red colorant, a beet red colorant, anthocyan, anthocyanin, phycocyan, phycocyanin, a chlorophyll colorant, and a combination thereof may be used, as the inorganic pigment, one selected from the group consisting of metal oxides, in particular, iron oxides (red, black, yellow, and brown), titanium dioxide, zinc oxide, chromium oxide, bismuth oxychloride, aluminum oxide, zirconium oxide, cobalt oxide, cerium oxide, nickel oxide, calcium hydroxide, iron hydroxide, aluminum hydroxide, chromium hydroxide, magnesium hydroxide, ferric ammonium ferrocyanide, Prussian blue, iron sulfide, manganese violet, carbon black, mica, kaolin, and a combination thereof may be used, and as the organic pigment, natural or synthetic organic dyes such as indigo lake, carmine lake, well known FD&C and D&C dye series-derived lakes, for example, D&C Red 21 aluminum lake, D&C Red 7 calcium lake, aromatic azo, indigoid, triphenylmethane, anthraquinone and xanthine dyes, and the like, may be used.

The cosmetic composition according to embodiments of the present invention may be a composition capable of being skin-externally, transdermally or subcutaneously administered, preferably, skin-externally or transdermally, and more preferably skin-externally administered, depending on an administration route. Particularly, since the cosmetic composition is used to prevent and treat skin aging, skin redness, and oxidation by photo-aging, such that the cosmetic composition is preferably a skin-external preparation.

Further, the cosmetic composition may contain a solvent generally contained in an application formulation thereof. For example, the cosmetic composition may contain one or more selected from ethanol, glycerin, butylene glycol, propylene glycol, polyethylene glycol, 1,2,4-butanetriol, sorbitol ester, 1,2,6-hexanetriol, benzyl alcohol, isopropanol, butanediol, diethylene glycol monoethylether, dimethyl isosorbide, N-methyl-2-pyrrolidone, propylene carbonate, glycereth-26, methyl gluceth-20, isocetyl myristate, isocetyl octanoate, octyldodecyl myristate, octyldodecanol, isostearyl isostearate, cetyl octanoate, neopentyl glycol dicaprate, and the like. In the case of preparing the cosmetic composition according to embodiments of the present invention using the solvent as described above, solubility of the compound in the solvent is slightly changed depending on a mixing ratio of the solvent. However, those skilled in the art to which the present invention pertains may suitably select and apply the kind of solvent and a use amount thereof depending on characteristics of a product.

In addition, the cosmetic composition may contain various materials for enhancing transdermal administration at the time of transdermally administering the cosmetic composition. For example, the cosmetic composition may contain a laurocapram derivative, oleic acid, ester derivatives of monooleate derivative, adapalene, tretinoin, retinaldehyde, tazarotene, salicylic acid, azelaic acid, glycolic acid, ethoxy diglycol, Tween 80, lecithin organogel, or the like. Further, in order to impart additional functions, the cosmetic composition according to embodiments of the present invention may contain auxiliary ingredients such as a cosurfactant, a surfactant, an anti-dandruff agent, a callus softener, a blood flow stimulant, a cell activator, a refreshing agent, a moisturizer, an antioxidant, a pH adjuster, purified water, or the like, as long as the effect of activating autophagy by the composition according to embodiments of the present invention is not inhibited. Depending on the application formulation, the cosmetic composition may contain suitable additives such as a perfume, a pigment, a preservative, an excipient, or the like.

The cosmetic composition according embodiments of to the present invention, which means a composition capable of being subcutaneously applied to the skin, the scalp, or the hair, and used to prepare all cosmetic products including basic cosmetics, makeup cosmetics, body products, shaving products, hair products, and the like, may be formulated into suspensions, emulsions, pastes, gels, creams, lotions, powders, soaps, surfactant-containing cleansing formulations, oil, powder foundations, emulsion foundations, wax foundations, or sprays, but the formulation of the cosmetic composition is not particularly limited.

More specifically, when the formulation of the cosmetic composition according to embodiments of the present invention is a paste, cream, or gel, animal oil, vegetable oil, wax, paraffin, starch, tragacanth, cellulose derivatives, polyethylene glycol, silicon, bentonite, silica, talc, zinc oxide, or the like, may be used as a carrier ingredient.

When the formulation of the cosmetic composition according to embodiments of the present invention is a powder or spray, lactose, talc, silica, aluminum hydroxide, calcium silicate, or polyamide powder may be used as a carrier ingredient. Particularly, when the formulation is spray, the cosmetic composition may additionally contain a propellant such as chlorofluorohydrocarbon, propane/butane, or dimethylether.

When the formulation of the cosmetic composition according to embodiments of the present invention is a solution or emulsion, a solvent, a solubilizer, or an emulsifier, may be used as a carrier ingredient. For example, water, ethanol, isopropanol, ethyl carbonate, ethyl acetate, benzyl alcohol, benzyl benzoate, propylene glycol, 1,3-butyl glycol oil, glycerol aliphatic ester, or polyethylene glycol or sorbitan fatty acid ester may be used as the carrier ingredient.

When the formulation of the cosmetic composition according to embodiments of the present invention is a suspension, liquid diluents such as water, ethanol, or propylene glycol, suspending agents such as ethoxylated isostearyl alcohols, polyoxyethylene sorbitol esters, and polyoxyethylene sorbitan esters, microcrystalline cellulose, aluminum meta-hydroxide, bentonite, agar, tragacanth, etc. may be used as a carrier ingredient.

When the formulation of the cosmetic composition according to embodiments of the present invention is a surfactant-containing cleansing formulation, aliphatic alcohol sulfate, aliphatic alcohol ether sulfate, sulphosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamide, vegetable oils, lanoline derivatives, ethoxylated glycerol fatty acid ester, or the like, may be used as a carrier ingredient.

When the formulation of the cosmetic composition according to embodiments of the present invention is the soap or surfactant-containing or surfactant-free cleansing formulation, the cosmetic composition may be wiped, peeled off, or washed with water after being applied onto the skin. A specific example of the soap may include liquid soap, powder soap, solid soap, or oil soap, a specific example of the surfactant-containing cleansing formulation may include cleansing foam, cleansing water, a cleansing towel, or a cleansing pack, and a specific example of the surfactant-free cleansing formulation may include a cleansing cream, a cleansing lotion, cleansing water, or a cleansing gel, but the present invention is not limited thereto.

Further, embodiments of the present invention provide a medicinal composition for preventing and treating skin inflammatory diseases caused by light, containing a compound inducing an increase in expression of adiponectin represented by Chemical Formula 1 according to embodiments of the present invention, or a pharmaceutically acceptable salt thereof as an active ingredient.

The compound inducing an increase in expression of adiponectin represented by Chemical Formula 1 according to embodiments of the present invention increases expression of adiponectin decreased in the skin photo-aged by light, particularly, UV light, while inducing autophagy activation, such that the medicinal composition is significantly effective in preventing and treating skin inflammation formed by exposure to light.

Preferably, the compound inducing an increase in expression of adiponectin represented by Chemical Formula 1 according to embodiments of the present invention may be represented by Chemical Formula 2, and contained in a content of 0.001 to 10 wt %, preferably, 0.001 to 1 wt % based on a total weight of the entire composition.

The pharmaceutically acceptable salt of the compound according to embodiments of the present invention may be prepared by a general method used in the art. As used herein, the term "pharmaceutically acceptable salt" includes salts derived from pharmaceutically acceptable inorganic acids, organic acids, or bases. A suitable example of the acid includes hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, trifluoroacetic acid, citric acid, methanesulfonic acid, formic acid, benzoic acid, malonic acid, naphthalane-2-sulfonic acid, benzene sulfonic acid, or the like. A salt derived from a suitable base may include an alkali metal such as sodium or the like, an alkali earth metal such as magnesium, or the like, ammonium, etc.

Mainly, the medicinal composition according to embodiments of the present invention may be orally, intravenously, intraperitoneally, intramuscularly, and subcutaneously administered. Further, the medicinal composition may be formulated into oral formulations such as powders, granules, tablets, capsules, suspensions, emulsions, syrups, aerosols, and the like, topical formulations, suppositories, sterile injection solutions, or the like, to thereby be used, but the formation of the medicinal composition is not particularly limited.

The medicinal composition according to embodiments of the present invention may additionally contain pharmaceutically acceptable additives generally used to prepare a medicinal composition. The term "pharmaceutically acceptable additive" means a carrier or a diluent that does not significantly stimulate living organism nor inhibit biological activity and properties of an administered compound. In addition, the additive may improve preparation, compactibility, appearance, and taste of the formulation. For example, if necessary, a stabilizer, a surfactant, a lubricant, a solubilizer, a buffer, a sweetener, a matrix, an adsorbent, a flavor enhancer a binder, a suspending agent, a hardener, an antioxidant, a brightener, a fragrance, a flavoring agent, pigment, a coating agent, a wetting agent, a moisture controlling agent, a filler, a defoaming agent, a refreshing agent, a masticating agent, an antistatic agent, a coloring agent, a sugar coating agent, an isotonic agent, a softener, an emulsifier, a tackifier, a thickener, a foaming agent, a pH adjusting agent, an excipient, a dispersant, a disintegrant, a waterproof agent, an antiseptic agent, a preservative, a solubilizing aid, a solvent, a fluidizing agent, or the like, may be added.

As an example, formulations for oral administration include tablets, pills, powders, granules, capsules, and the like, and these formulations may contain at least one excipient and/or lubricant, etc. Liquid formulations for oral administration include suspensions, solutions, emulsions, syrups, and the like, and these liquid preparations may contain various excipients such as a wetting agent, a sweetener, a flavoring agent, a preservative, or the like, as well as water and liquid paraffin that are generally used simple diluents. In addition, formulations for parenteral administration include sterile aqueous solutions, non-aqueous solvents, suspensions, emulsions, freeze-dried formulations, suppositories, and the like.

A preferable administration dose of the medicinal composition may be changed depending on a state and weight of a patient, a degree of disease, a drug formulation, and an administration route and duration, but be appropriately selected by those skilled in the art. In order to obtain a more preferable effect, a daily administration dose of the composition according to embodiments of the present invention may be preferably 0.1 mg/kg to 100 mg/kg based on the active ingredient, but is not limited thereto. One dose may be administered once a day, or divided into several doses and then administered several times. A pharmaceutical administration form of the medicinal composition according to embodiments of the present invention may be a form of a pharmaceutically acceptable salt of the active ingredient. Further, the medicinal composition may be used alone, or a suitable set as well as a combination of the medicinal composition with another pharmaceutically active compound may also be used.

The medicinal composition according to embodiments of the present invention may be orally or parenterally administered, and in the case of parenteral administration, the medicinal composition may be intravenously, subcutaneously, intramuscularly, and intraperitoneally injected, or transdermally administered.

The medicinal composition according to embodiments of the present invention may contain a pharmaceutically acceptable carrier. The pharmaceutically acceptable carrier contained in the medicinal composition according to embodiments of the present invention, which is generally used at the time of preparation, includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, and the like, but is not limited thereto. The medicinal composition according to embodiments of the present invention may additionally contain a lubricant, a wetting agent, a sweetener, a flavoring agent, an emulsifier, a suspending agent, a preservative, or the like, in addition to the above ingredients.

The medicinal composition according to embodiments of the present invention may be prepared in a unit dose form or prepared in a form in which the medicinal composition is input into a multi-dose container by being formulated in a general formulation using the pharmaceutically acceptable carrier and/or the excipient according to a method capable of being easily performed by those skilled in the art to which the present invention pertains. The general formulation means, for example, oral formulations (tablets, capsules, powders) and formulations for sublingual, rectal, intravaginal, nasal, topical, or parenteral administration formulations (including intravenous, intracavernosal, intramuscular, subcutaneous, and intratubular administration formulations). For example, the compound inducing autophagy activation according to embodiments of the present invention may be orally or sublingually administered in a form of a tablet containing starch or lactose, a capsule containing only the compound according to embodiments of the present invention or containing an excipient in addition to the compound, or an elixir or suspension containing a chemical for flavor or color. A liquid formulation is prepared together with a pharmaceutically acceptable additive such as a suspending agent (for example, methylcellulose, semi-synthetic glycerides such as Witepsol, a mixture of apricot kernel oil and polyethylene glycol (PEG)-6 ester, or a glyceride mixture such as a mixture of PEG-8 and caprylic/capric glyceride). Further, in the case in which the medicinal composition is parenterally, for example, intravenously, intracavernosally, intramuscularly, subcutaneously, and intratubularly injected, it is most preferable that the medicinal composition is used in a form of a sterile aqueous solution. In this case, the solution may contain other materials (for example, salts, mannitol, or monosaccharides such as glucose) so as to be isotonic with blood.

The medicinal composition according to the embodiment of the present invention may be used in a form of tablets, pills, capsules, granules, powders, solutions, patches, or injections.

Hereinafter, embodiments of the present invention will be described in detail through Examples. However, the following Examples are to illustrate embodiments of the present invention, and the scope of the present invention is not limited to the following Examples.

[Example 1] Synthesis of Compound 1

Example 1-1. Synthesis of Compound 1a

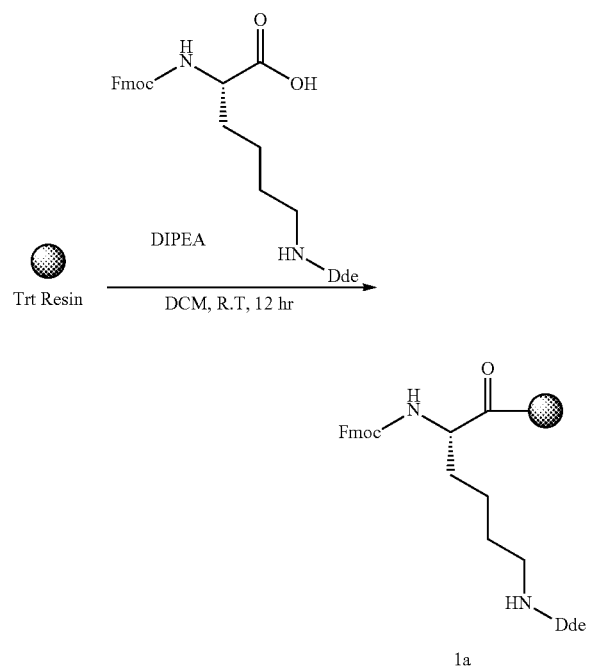

1a

In an 800 ml reaction vessel, 2-chloro trityl chloride resin (100-200 mesh, Novabiochem, 20 g, 1 equivalent) and Fmoc-Lys(Dde)-OH(Nα-Fmoc-Nε-Dde-L-lysine,Nα-Fmoc-Nε-[1-(4,4-dimethyl-2,6-dioxocyclohexylidene) ethyl]-L-lysine) (21.3 g, 2 equivalents), and DIPEA (29.9 ml, 8 equivalents) were put into dichloromethane (DCM, 700 ml) and reacted with each other at room temperature for 12 hours. Then, a reaction solution was removed by filtering, and a synthesized resin was sequentially washed with a dichloromethane (DCM, 500 ml), MeOH (500 ml), DCM (500 ml), and dimethylformamide (DMF, 500 ml). The resultant was dried under vacuum, thereby obtaining Compound 1a (Fmoc-Lys(Dde)-O-2-chloro trityl resin, 23 g, yield 99%) as a solid phase.

Example 1-2. Synthesis of Compound 1b

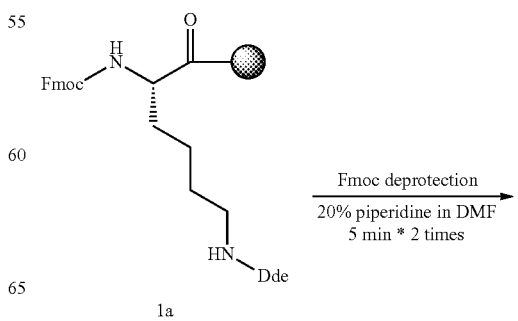

1a

Fmoc deprotection
20% piperidine in DMF
5 min * 2 times

15

-continued

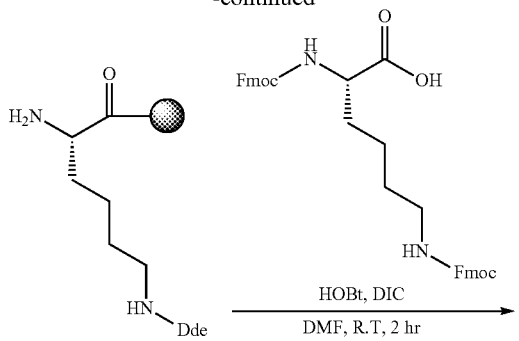

After Compound 1a and 20% piperidine in DMF (700 ml) were put into an 800 ml reaction vessel and reacted with each other at room temperature for 5 minutes, a reaction solution was removed by filtering. 20% piperidine in DMF (700 ml) was added thereto again, and a reaction was carried out at room temperature for 5 minutes. A reaction solution was removed by filtering, and a synthesized resin was sequentially washed with DCM (500 ml), MeOH (500 ml), DCM (500 ml), and DMF (500 ml). Fmoc-Lys(Fmoc)-OH (47.3 g, 4 equivalents), HOBt (10.8 g, 4 equivalents), and DIC (12.4 ml, 4 equivalents) were dissolved in DMF (600 ml) and added to a product formed by drying the resultant under vacuum to remove solid phase Fmoc, and a reaction was carried out at room temperature for 4 hours. A reaction solution was removed by filtering, and a synthesized resin was sequentially washed with DCM (500 ml), MeOH (500 ml), DCM (500 ml), and DMF (500 ml). The resultant was dried under vacuum, thereby obtaining Compound 1b (Fmoc-Lys(Fmoc)-Lys(Dde)-O-2-chloro trityl resin, 25 g, yield: 98%) as a solid phase.

16

Example 1-3. Synthesis of Compound 1c

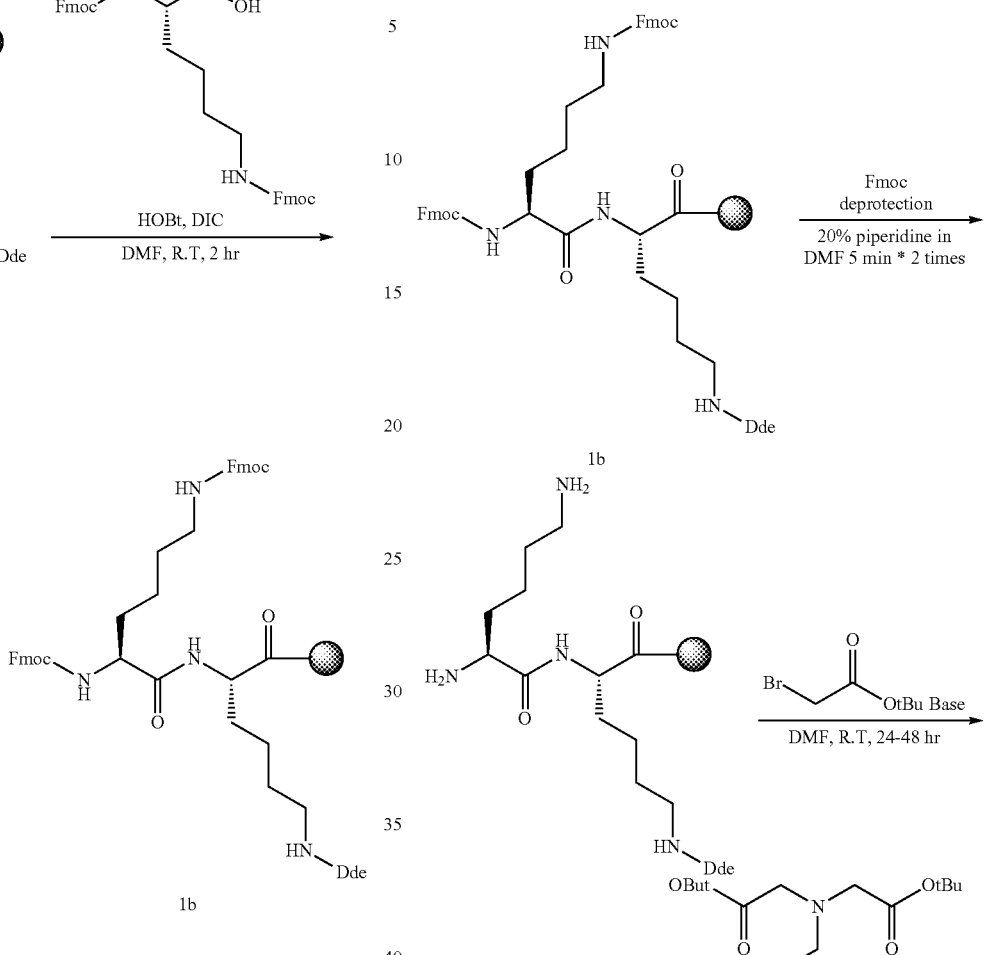

Base:
i) DIPEA
ii) 1,8-Bis(dimethylamino)napthalene

After Compound 1b and 20% piperidine in DMF (700 ml) were put into an 800 ml reaction vessel and reacted with each other at room temperature for 5 minutes, a reaction solution was removed by filtering. 20% piperidine in DMF (700 ml) was added thereto again, and a reaction was carried out at room temperature for 5 minutes. A reaction solution was removed by filtering, and a synthesized resin was sequentially washed with DCM (500 ml), MeOH (500 ml), DCM (500 ml), and DMF (500 ml). tert-butyl bromoacetate (59.1 ml, 20 equivalents) and DIPEA (69.7 ml, equivalents) were dissolved in DMF (600 ml) and added to a product formed by drying the resultant under vacuum to remove solid phase Fmoc, and a reaction was carried out at room temperature for 12 hours. A reaction solution was removed by filtering, and a synthesized resin was washed with DMF (500 ml). Again, 1,8-Bis(dimethylamino)napthalene (85.7 g, 20 equivalents), tert-butyl bromoacetate (59.1 ml, 20 equivalents), and DIPEA (69.7 ml, 20 equivalents) were dissolved in DMF (600 ml) and added thereto, and a reaction was carried out at room temperature for 12 hours. A reaction solution was removed by filtering, and a synthesized resin was sequentially washed with DCM (500 ml), MeOH (500 ml), DCM (500 ml), and DMF (500 ml). The resultant was dried under vacuum, thereby obtaining Compound 1c (tert-butoxycarbonylmethyl)$_2$-Lys(tert-butoxycarbonylmethyl)$_2$-Lys(Dde)-O-2-chloro trityl resin, 31 g, yield: 95%) as a solid phase.

Example 1-4. Synthesis of Compound 1d

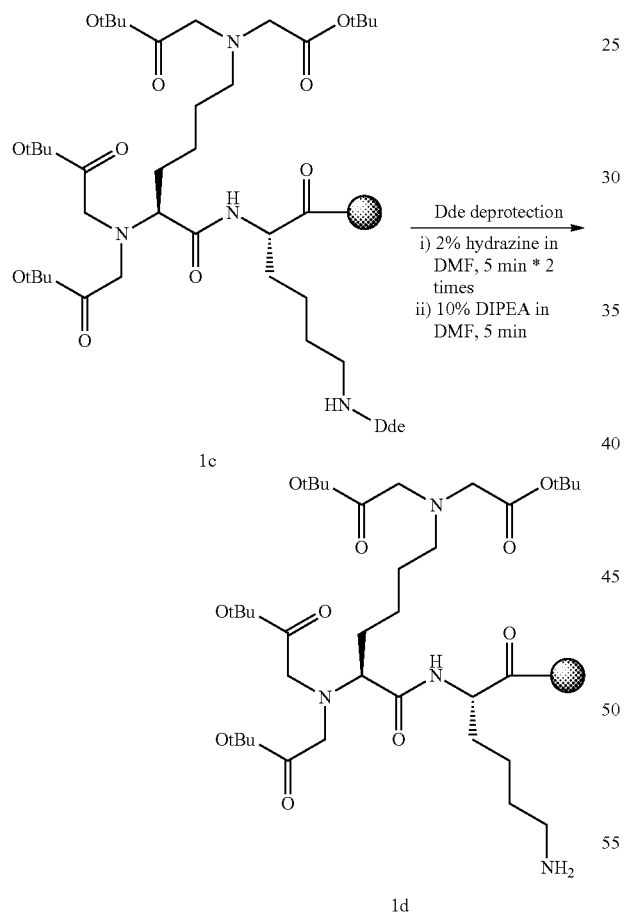

Compound 1c and 2% hydrazine in DMF (700 ml) were put into an 800 ml reaction vessel and reacted with each other at room temperature for 5 minutes. A reaction solution was removed by filtering, and a synthesized resin was washed with DMF (500 ml) Again, 10% DIPEA in DMF (700 ml) was added thereto, and a reaction was carried out at room temperature for 5 minutes. A reaction solution was removed by filtering, and a synthesized resin was sequentially washed with DCM (500 ml), MeOH (500 ml), DCM (500 ml), and DMF (500 ml). The resultant was dried under vacuum, thereby obtaining Compound 1d (tert-butoxycarbonylmethyl)$_2$-Lys (tert-butoxycarbonylmethyl)$_2$-Lys (NH$_2$)—O-2-chloro trityl resin, 30 g, yield: 99%) as a solid phase.

Example 1-5. Synthesis of Compound 1

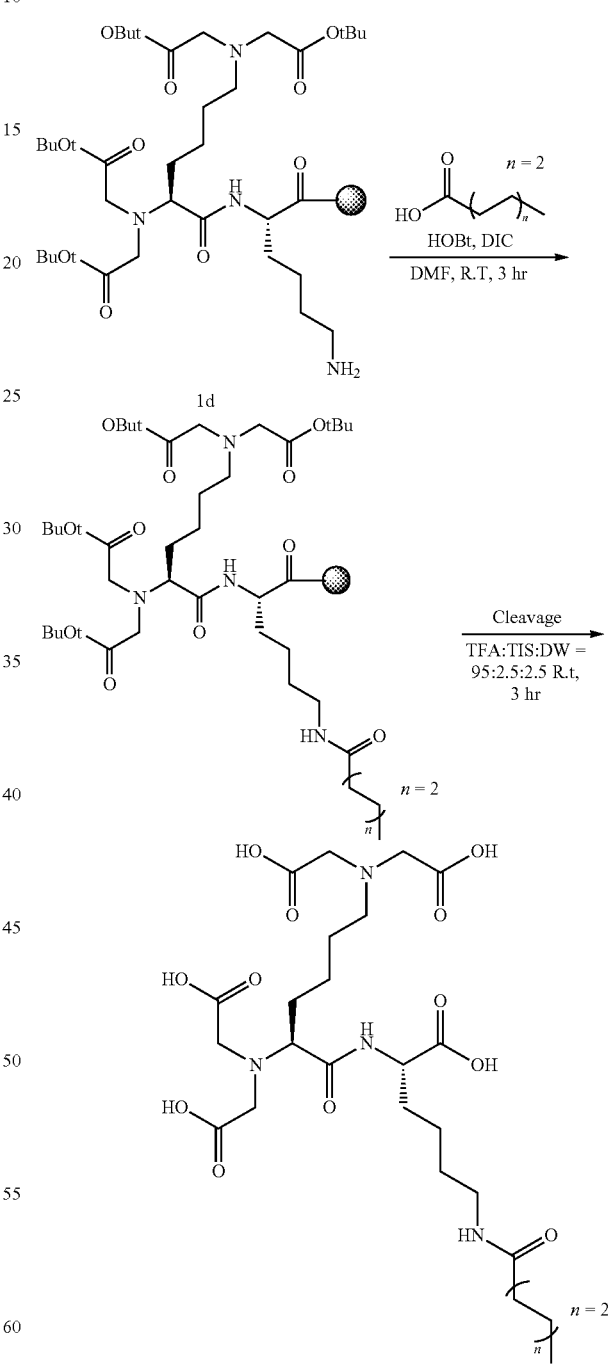

Compound 1d (460 mg, 1 equivalent) was put into a 10 ml reaction vessel, hexanoic acid (186 ul, 8 equivalents), DIC (248 ul, 8 equivalents), and HOBt (216 mg, 8 equivalents)

were dissolved in DMF (5 ml) and added thereto, and a reaction was carried out at room temperature for 2 hours. A reaction solution was removed by filtering, and a synthesized resin was sequentially washed with DCM (5 ml), MeOH (5 ml), and DCM (5 ml). After the resultant was dried under vacuum, cleavage cocktail (5 ml, trifluoro acetic acid:triisopropylsilane:DW=95:2.5:2.5) was added thereto, and a reaction was carried out at room temperature for 3 hours. A reaction solution was collected by filtering, and diethyl ether (45 ml) was added thereto to precipitate a product. A solid product was collected using a centrifugal separator, and the collected solid product was washed twice with diethyl ether (45 ml). The obtained solid product was purified using a Prep-HPLC (column C18, 10 um, 250 mm×22 mm) and freeze-dried, thereby obtaining Compound 1 (molecular weight measured by LC-Mass: 604.65, 77 mg, yield: 64%).

[Comparative Example 1] Synthesis of Compound 2

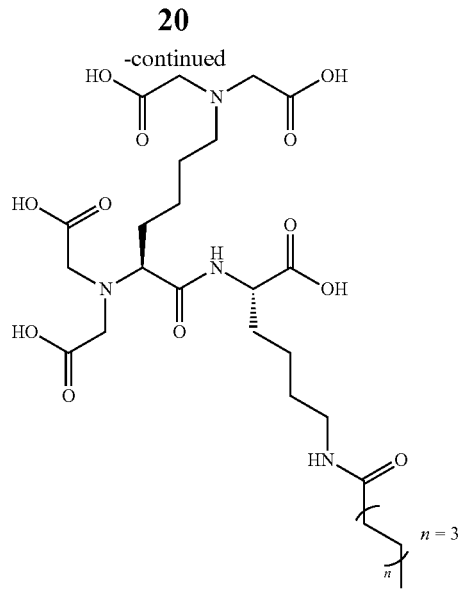

2

Compound 1d (460 mg, 1 equivalent) was put into a 10 ml reaction vessel, octanoic acid (230 ul, 8 equivalents), DIC (248 ul, 8 equivalents), and HOBt (216 mg, 8 equivalents) were dissolved in DMF (5 ml) and added thereto, and a reaction was carried out at room temperature for 2 hours. A reaction solution was removed by filtering, and a synthesized resin was sequentially washed with DCM (5 ml), MeOH (5 ml), and DCM (5 ml). After the resultant was dried under vacuum, cleavage cocktail (5 ml, trifluoro acetic acid:triisopropylsilane:DW=95:2.5:2.5) was added thereto, and a reaction was carried out at room temperature for 3 hours. A reaction solution was collected by filtering, and diethyl ether (45 ml) was added thereto to precipitate a product. A solid product was collected using a centrifugal separator, and the collected solid product was washed twice with diethyl ether (45 ml). The obtained solid product was purified using a Prep-HPLC (column C18, 10 um, 250 mm×22 mm) and freeze-dried, thereby obtaining Compound 2 (molecular weight measured by LC-Mass: 632.7, 62 mg, yield: 56%).

[Comparative Example 2] Synthesis of Compound 3

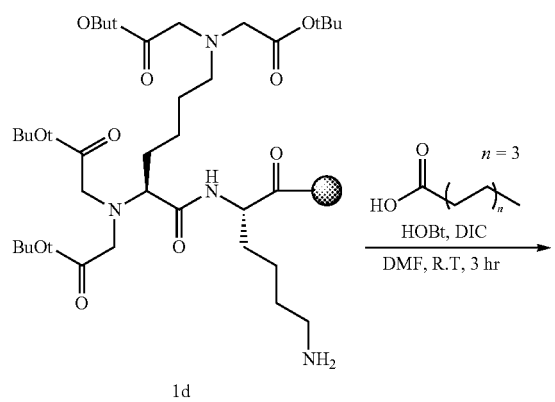

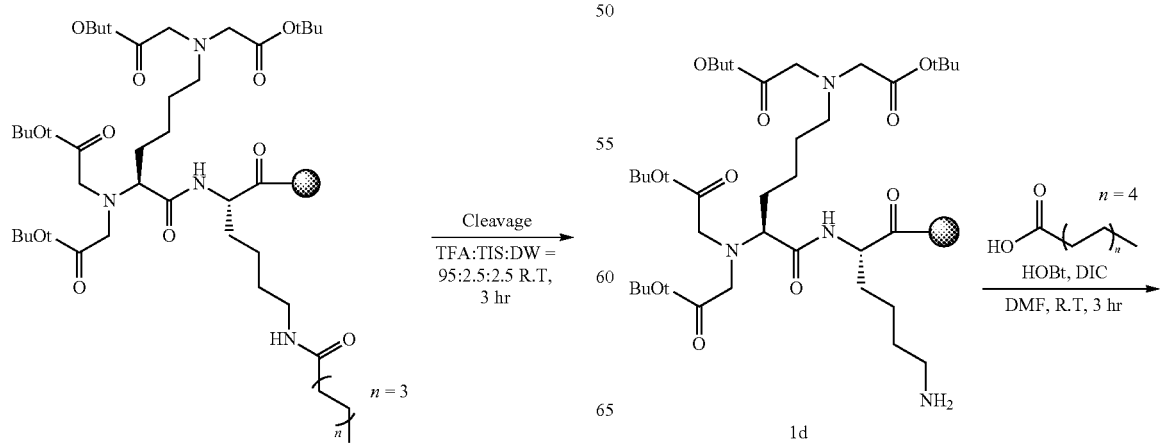

[Comparative Example 3] Synthesis of Compound 4

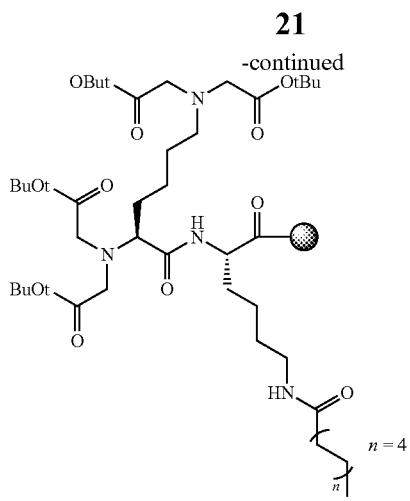

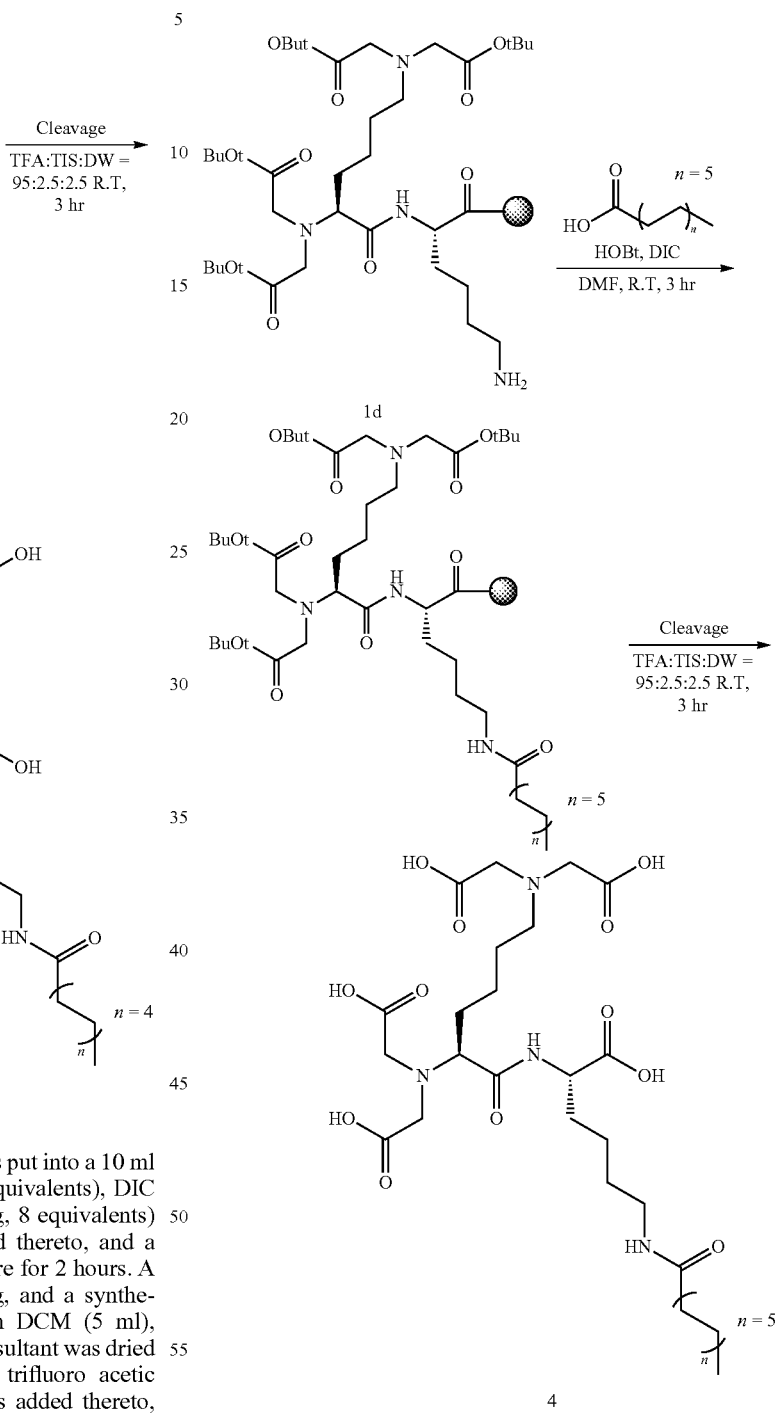

Compound 1d (460 mg, 1 equivalent) was put into a 10 ml reaction vessel, decanoic acid (275 ul, 8 equivalents), DIC (248 ul, 8 equivalents), and HOBt (216 mg, 8 equivalents) were dissolved in DMF (5 ml) and added thereto, and a reaction was carried out at room temperature for 2 hours. A reaction solution was removed by filtering, and a synthesized resin was sequentially washed with DCM (5 ml), MeOH (5 ml), and DCM (5 ml). After the resultant was dried under vacuum, cleavage cocktail (5 ml, trifluoro acetic acid:triisopropylsilane:DW=95:2.5:2.5) was added thereto, and a reaction was carried out at room temperature for 3 hours. A reaction solution was collected by filtering, and diethyl ether (45 ml) was added thereto to precipitate a product. A solid product was collected using a centrifugal separator, and the collected solid product was washed twice with diethyl ether (45 ml). The obtained solid product was purified using a Prep-HPLC (column C18, 10 um, 250 mm×22 mm) and freeze-dried, thereby obtaining Compound 3 (molecular weight measured by LC-Mass: 660.36, 79 mg, yield: 66%).

Compound 1d (460 mg, 1 equivalent) was put into a 10 ml reaction vessel, dodecanoic acid (320 ul, 8 equivalents), DIC (248 ul, 8 equivalents), and HOBt (216 mg, 8 equivalents) were dissolved in DMF (5 ml) and added thereto, and a reaction was carried out at room temperature for 2 hours. A reaction solution was removed by filtering, and a synthesized resin was sequentially washed with DCM (5 ml), MeOH (5 ml), and DCM (5 ml). After the resultant was dried under vacuum, cleavage cocktail (5 ml, trifluoro acetic acid:triisopropylsilane:DW=95:2.5:2.5) was added thereto, and a reaction was carried out at room temperature for 3 hours. A reaction solution was collected by filtering, and diethyl ether (45 ml) was added thereto to precipitate a product. A solid product was collected using a centrifugal separator, and the collected solid product was washed twice with diethyl ether (45 ml). The obtained solid product was purified using a Prep-HPLC (column C18, 10 um, 250 mm×22 mm) and freeze-dried, thereby obtaining Compound 4 (molecular weight measured by LC-Mass: 688.81, 72 mg, yield: 62%).

[Example 2] Increase in Autophagy Activity by Compound 1 According to Embodiments of Present Invention In order to analyze an increase in autophagy activity in cells by treatment of Compound 1 of embodiments of the present invention, western blot for light chain 3 (LC3) protein was performed.

As a specific experimental method, human dermal fibroblasts (HDF) were seeded onto a 6-well culture plate ($1\times10^5$ cells/well) and cultured in a dermal fibroblast growth medium (DF-1 medium, Zenbio) in an incubator at 37° C. under 5% $CO_2$ atmosphere for 24 hours. Compound 1 of embodiments of the present invention was dissolved in water at a concentration of 100 mM to prepare a condensate, the condensate was diluted with a medium at a concentration of 200 uM, and a diluted solution was put into and treated in each of the wells (1 ml/well) in a state in which 1 ml of the medium was filled in advance in each of the wells, followed by culturing for a predetermined time. After the culturing was terminated, the medium was removed and cells were disrupted using a sodium dodecyl sulfate (SDS) sample buffer. Then, respective proteins were isolated by sodium dodecyl sulfate-polyacrylamide gel electrophoresis (SDS-PAGE) and transferred to a polyvinylidene difluoride (PVDF) membrane, and non-specific binding was eliminated using a blocking buffer. After reacting the resultant with an antibody against the LC3 protein and a HRP-conjugatedsecondary antibody thereof (anti-rabbit IgG HRP, Sigma), ChemiDoc (UVITEC) analysis was performed by performing an enhanced chemiluminescence (ECL) reaction using an ECL prime kit (Amersham Pharmacia).

The result was illustrated in FIG. 1, and as illustrated in FIG. 1, it may be appreciated that formation of Microtubule-associated protein 1A/1B-light chain 3 (LC3-II) was increased by Compound 1 of embodiments of the present invention.

[Example 3 and Comparative Example 4] Increases in Expression of Adiponectin by Compound 1 According to Embodiments of Present Invention and Compound 4 of Comparative Example 3

In order to compare and analyze increases in expression of adiponectin in cells by treatment of Compound 1 of embodiments of the present invention and Compound 4 of Comparative Example 3, real-time polymerase chain reaction (PCR) for an adiponectin gene was performed.

As a specific experimental method, human dermal fibroblasts (HDF) were seeded onto a 6-well culture plate ($1\times10^5$ cells/well) and cultured in a dermal fibroblast growth medium (DF-1 medium, Zenbio) in an incubator at 37° C. under 5% $CO_2$ atmosphere for 24 hours. Compound 1 and Compound 4 of embodiments of the present invention were each dissolved in water at a concentration of 100 mM to prepare a condensate, the condensate was diluted with a medium at a concentration of 200 uM, and a diluted solution was put into and treated in each of the wells (1 ml/well) in a state in which 1 ml of the medium was filled in advance in each of the wells, followed by culturing for 24 hours. After the culturing was terminated, the medium was removed, 1 ml of a dermal fibroblast basal medium (DF-2 medium, Zenbio) was added thereto, and each of the wells was irradiated with ultraviolet A (UVA) light at 10 $J/cm^2$. Again, each of the wells was treated with Compound 1 or Compound 4 in the same manner, followed by additional culturing for 24 hours. After the culturing was terminated, the cells were disrupted by Trizol (Ambion), an entire mRNA was collected using chloroform/isopropanol, cDNA was synthesized using reverse transcriptase, and real-time PCR (QuantStudio 3, Thermo Fisher) was performed using a primer specific to adiponectin. The results were illustrated in FIGS. 2 and 3.

As illustrated in FIGS. 2 and 3, it was confirmed that expression of the adiponectin gene was increased by treatment of Compound 1 according to embodiments of the present invention. Further, it was confirmed that an expression amount of the adiponectin gene decreased after UVA irradiation was further recovered after treatment of Compound 1 of embodiments of the present invention as compared to Compound 4.

[Example 4 and Comparative Example 5] Decrease in Expression of MMP-1 by Compound 1 According to Embodiments of Present Invention In order to compare and analyze an effect of decreasing expression of matrix metalloproteinase-1 (MMP-1) by treatment of Compound 1 or Compound 4 of embodiments of the present invention, quantitative polymerase chain reaction (qPCR) for a MMP-1 gene was performed after irradiating ultraviolet A (UVA) light and ultraviolet B (UVB) light to cells.

As a specific experimental method, human dermal fibroblasts (HDF) were seeded onto a 6-well culture plate ($1\times10^5$ cells/well) and cultured in a dermal fibroblast growth medium (DF-1 medium, Zenbio) in an incubator at 37° C. under 5% $CO_2$ atmosphere for 24 hours. Compound 1 and Compound 4 of embodiments of the present invention were each dissolved in water at a concentration of 100 mM to prepare a condensate, the condensate was diluted with a medium at a concentration of 200 uM, and a diluted solution was put into and treated in each of the wells (1 ml/well) in a state in which 1 ml of the medium was filled in advance in each of the wells, followed by culturing for 24 hours. In a UV light treatment group, after the medium was replaced with a dermal fibroblast basal medium (DF-2 medium, Zenbio), each of the well was irradiated with the UVB light (100 $mJ/cm^2$) or UVA light (5 $J/cm^2$), followed by additional culturing for 24 hours. After the culturing was terminated, the cells were disrupted by Trizol (Ambion), an entire mRNA was collected using chloroform/isopropanol, cDNA was synthesized using reverse transcriptase, and real-time (RT) PCR (QuantStudio 3, Thermo Fisher) was performed using a primer specific to MMP-1. The results were illustrated in FIG. 4.

As illustrated in the result of FIG. 4, it may be appreciated that after treatment of Compound 1 of embodiments of the present invention, an expression amount of the MMP-1 gene increased after UVA and UVB light was irradiated was decreased, and the effect of decreasing expression of MMP-1 was more excellent as compared to AdipoRon (adiponectin receptor agonist) used as a control. Further, an expression decrease amount of the MMP-1 was further increased as compared to treatment of Compound 4 of Comparative Example 3. Therefore, Compound 1 of embodiments of the present invention may decrease decomposition of collagen protein caused by UV light of sun light, thereby making it possible to suppress formation of wrinkles caused by photo-aging.

[Example 5 and Comparative Example 6] Decrease in Expression and Secretion of IL-6 by Compound 1 According to Embodiments of Present Invention In order to compare and analyze an effect of decreasing expression of interleukin 6 (IL-6) corresponding to an inflammatory cytokine by treatment of Compound 1 or Compound 4 of embodiments of the present invention, ultraviolet B (UVB) light was irradiated to cells, and then, RT-PCR for IL-6 gene and enzyme-linked immunosorbent assay (ELISA) for IL-6 were performed.

As a specific experimental method, human epidermal keratinocytes (adult) derived from human were seeded onto a 12-well culture plate ($2 \times 10^5$ cells/well) and cultured in an EpiLife medium (Gibco, 1× Human keratinocyte growth supplement, 1× antibiotics) in an incubator at 37° C. under 5% $CO_2$ atmosphere for 24 hours. Compound 1 and Compound 4 of embodiments of the present invention were each dissolved in water at a concentration of 100 mM to prepare a condensate, the condensate was diluted with a medium at a concentration of 200 uM, and a diluted solution was put into and treated in each of the wells (0.5 ml/well) in a state in which 0.5 ml of the medium was filled in advance in each of the wells, followed by culturing for 24 hours. Thereafter, the medium was replaced with a growth supplement-free medium, ultraviolet B (UVB) light was irradiated at 30 mJ/cm$^2$, followed by additional culturing for 24 hours. After the culturing was terminated and the medium was collected, the cells were disrupted by Trizol (Ambion), an entire mRNA was collected using chloroform/isopropanol, cDNA was synthesized using reverse transcriptase, and RT-PCR (Thermal Cycler, Bio-rad) was performed using a primer specific to IL-6. After performing the PCR, the resultant was analyzed using agarose gel electrophoresis, and the results were illustrated in FIG. 5. Further, ELISA analysis for IL-6 was performed on the collected medium, and the results were illustrated in FIG. 6.

As illustrated in FIG. 5, it was confirmed that after treatment of Compound 1 of embodiments of the present invention, expression of the IL-6 gene increased after UVB light irradiation tended to be decreased as compared to a blank, and an effect of decreasing expression was more excellent than AdipoRon used as the control. In addition, the effect of decreasing expression of the IL-6 gene was more excellent as compared to treatment of Compound 4 of Comparative Example 3. In FIG. 6, it was confirmed that after treatment of Compound 1 of embodiments of the present invention, secretion of IL-6 increased after UVB light irradiation was decreased as compared to the blank. Therefore, it may be appreciated that the present Compound 1 is effective in alleviating inflammation caused by UV light of sun light.

[Example 6 and Comparative Example 7] Decrease in Secretion of IL-8 by Compound 1 and Compound 4 According to Embodiments of Present Invention In order to compare and analyze an effect of decreasing secretion of interleukin 8 (IL-8) corresponding to an inflammatory cytokine by treatment of Compound 1 or Compound 4 of embodiments of the present invention, ultraviolet B (UVB) light was irradiated to cells, and then, ELISA analysis for IL-8 was performed.

As a specific experimental method, human epidermal keratinocytes (adult) derived from human were seeded onto a 12-well culture plate ($2 \times 10^5$ cells) and cultured in an EpiLife medium (Gibco, 1× Human keratinocyte growth supplement, 1× antibiotics) in an incubator at 37° C. under 5% $CO_2$ atmosphere for 24 hours. Compound 1 of embodiments of the present invention and Compound 4 were each dissolved in water at a concentration of 100 mM to prepare a condensate, the condensate was diluted with a medium at a concentration of 200 uM, and a diluted solution was put into and treated in each of the wells (0.5 ml/well) in a state in which 0.5 ml of the medium was filled in advance in each of the well, followed by culturing for 24 hours. Thereafter, the medium was replaced with a growth supplement-free medium, ultraviolet B (UVB) light was irradiated at 100 mJ/cm$^2$, followed by additional culturing for 24 hours. After the culturing was terminated and the medium was collected, ELISA analysis for IL-8 was performed, and the results were illustrated in FIG. 7.

As illustrated in FIG. 7, it was confirmed that after treatment of Compound 1 of embodiments of the present invention, secretion of IL-8 increased after UVB light irradiation was decreased as compared to a blank. In addition, secretion of IL-8 was significantly decreased as compared to treatment of Compound of Comparative Example 3. Therefore, it may be appreciated that the present Compound 1 is effective in alleviating inflammation caused by UV light of sun light.

[Example 7] Increase in Formation of Adiponectin Due to Autophagy Activation of Compound 1 According to Embodiments of Present Invention In order to compare and analyze an increase in formation of adiponectin and an increase in autophagy activity by treatment of Compound 1 of embodiments of the present invention, 3-methyladenine (3-MA) and chloroquine (CQ) corresponding to autophagy inhibitors were treated in cells, and western blot for adiponectin protein was performed.

As a specific experimental method, human dermal fibroblasts (HDF, neonatal) were seeded onto a 6-well culture plate ($1 \times 10^5$ cells/well) and cultured in a medium 106 (Gibco) containing low serum growth supplement (LSGS, Gibco) in an incubator at 37° C. under 5% $CO_2$ atmosphere for 24 hours. Compound 1 of embodiments of the present invention was dissolved in water at a concentration of 100 mM to prepare a condensate, and the condensate was diluted with the medium at a concentration of 300 uM. Further, 3-MA and CQ were dissolved in water at concentrations of 50 mM and 10 mM to prepare condensates, respectively, the condensates were diluted with the medium at concentrations of 15 mM and 30 uM respectively. Then, after each of the wells was treated with these materials at concentrations finally diluted three times, respectively, culturing was performed for 48 hours. After the culturing was terminate, the medium was removed, and the cells were disrupted by a SDS sample buffer. After respective proteins were isolated by SDS-PAGE gel electrophoresis and transferred to a polyvinylidene difluoride (PVDF) membrane, non-specific binding was eliminated using a blocking buffer. After reacting the resultant with an antibody against the LC3 protein and a HRP-conjugated secondary antibody thereof (anti-rabbit IgG HRP, Sigma), ChemiDoc (UVITEC) analysis was performed by performing an enhanced chemiluminescence (ECL) reaction using an ECL prime kit (Amersham Pharmacia).

The results were illustrated in FIG. 8, and as illustrated in FIG. 8, it was confirmed that formation of the adiponectin protein was increased by Compound 1 of embodiments of the present invention, and after treatment together with the autophagy inhibitors, formation of the adiponectin protein increased by Compound 1 was decreased. Therefore, it may be appreciated that an increase in formation of the adiponectin protein by Compound 1 was caused by the autophagy activity.

[Example 8] Effect of Protecting Cell DNA Damage by Compound 1 According to Embodiments of Present Invention It was known that cyclobutane pyrimidine dimmers (CPD), which are products of C=C double bond between thymine or cytosine bases of DNA by ultraviolet B (UVB), changes a structure of the DNA to consequently suppress polymerase and replication, and ultimately act as a main cause of human melanoma.

In order to confirm an effect of protecting cell DNA damage by Compound 1 of embodiments of the present invention, formation of CPD was analyzed by performing enzyme-linked immunosorbent assay (ELISA) and confocal microscopy using immunofluorescence staining.

As a specific experimental method, human dermal fibroblasts (HDF, neonatal) were seeded onto a 96-well culture plate or a poly-L-Lys coated confocal slide ($3\times10^4$ to $4\times10^4$ cells/well or slide) and cultured in a medium 106 (Gibco) containing low serum growth supplement (LSGS, Gibco) in an incubator at 37° C. under 5% $CO_2$ atmosphere for 24 hours. Compound 1 of embodiments of the present invention was dissolved in water at a concentration of 100 mM to prepare a condensate, the condensate was diluted with a LSGS-free medium at a concentration of 200 uM, and a diluted solution was put into and pre-treated in each of the wells (0.1 ml/well) in a state in which 0.1 ml of the medium was filled in advance in each of the well, followed by culturing for 24 hours. Thereafter, after replacement with PBS, ultraviolet B (UVB) light was irradiated at 100 mJ/cm$^2$, and Compound 1 diluted in the same manner as described above was post-treated again, followed by additional culturing for 24 hours. After the culturing was terminated, CPD ELISA and CPD staining were performed using a commercially available kit (OxiSelect™, Cell biolabs) according to the methods described in manufacturer's manuals.

As a result, as illustrated in FIG. 9, it may be appreciated that formation of CPD increased after UVB light irradiation was decreased by treatment of Compound 1 of embodiments of the present invention. Further, as illustrated in FIG. 10, it was confirmed that an intensity of green fluorescence increased after UVB light irradiation was decreased after treatment of Compound 1 of embodiments of the present invention. Therefore, it may be appreciated that Compound 1 of embodiments of the present invention is effective in repairing DNA damage caused by UV light to thereby protect cells.

[Example 9] Effect of Repairing Cell DNA Damage by Compound 1 According to Embodiments of Present Invention As main factors of a nucleotide excision repair (NER) pathway corresponding to repairing mechanism of damaged DNA, there are xeroderma pigmentosum, complementation groups A and C (XPA and XPC), wherein XPC serves to sense a DNA damage site and XPA serves as a supporter for collecting DNA repairing proteins to the DNA damage site.

In order to confirm an effect of repairing cell DNA damage by Compound 1 of embodiments of the present invention, changes in expression of xeroderma pigmentosum, complementation groups A and C (XPA and XPC) genes were confirmed using qPCR.

As a specific experimental method, human dermal fibroblasts (HDF, neonatal) were seeded onto a 6-well culture plate ($1\times10^5$ cells/well) and cultured in a medium 106 (Gibco) containing low serum growth supplement (LSGS, Gibco) in an incubator at 37° C. under 5% $CO_2$ atmosphere for 24 hours. Compound 1 of embodiments of the present invention was dissolved in water at a concentration of 100 mM to prepare a condensate, the condensate was diluted with the medium at a concentration of 200 uM, and a diluted solution was put into and pre-treated in each of the wells (0.1 ml/well) in a state in which 0.1 ml of the medium was filled in advance in each of the well, followed by culturing for 24 hours. Thereafter, after replacement with PBS, ultraviolet B (UVB) light was irradiated at 100 mJ/cm$^2$, and Compound 1 diluted in the same manner as described above was post-treated again, followed by additional culturing for 24 hours. After the culturing was terminated, the culture medium was removed, an entire mRNA was collected using a RNeasy Mini Kit (Qiagen), cDNA was synthesized using reverse transcriptase, and real-time PCR (QuantStudio 3, Thermo Fisher) was performed using primers specific to XPC and XPA.

As a result, as illustrated in FIG. 11, it was confirmed that expression of the XPC and XPA genes decreased after UVB light irradiation was increased after treatment of Compound 1 of embodiments of the present invention. Therefore, it may be appreciated that Compound 1 of embodiments of the present invention has an effect of repairing cells from DNA damage caused by UV light.

[Example 10] Effect of Preventing UV-Induced Skin Damage by Compound 1 According to Embodiments of Present Invention In order to confirm an effect of protecting the skin by Compound 1 of embodiments of the present invention against UV light, a clinical test for a product containing Compound 1 of embodiments of the present invention was performed through Seowon Skin Research Center (SSRC).

As a specific test method, a product using Cetaphil daily facial moisturizer (SPF15/PA++, Galderma Korea) as a vehicle and containing Compound 1 of embodiments of the present invention at a content of 100 ppm, that is, 0.01 wt % was prepared, and the product was applied onto the inside of the forearm (from the elbow to the wrist) of 13 subjects (average age: 27.0±10.4) twice a day for a total of 2 weeks. Then, UV light was irradiated using a UV solar simulator (WACOM, Japan) and a UV light meter (Sato Shouji, Japan), and an increase rate of a minimal erythema dose (MED), that is, a minimal dose of UV light irradiation causing erythema, was measured, thereby determining the effect.

The result was illustrated in FIG. 12, and as illustrated in FIG. 12, as a result of determining the MED, after using the product containing Compound 1 of embodiments of the present invention for 2 weeks, MED was statically significantly increased as compared to 0 week before using the product, and the increase rate (%) of MED was averagely increased by 56.2% after using the product containing Compound 1 of embodiments of the present invention for 2 weeks as compared to 0 week before using the product. Therefore, it may be appreciated that Compound 1 of embodiments of the present invention is effective in preventing skin damage caused by UV light.

[Example 11] Effect of Alleviating Skin Redness by Compound 1 According to Embodiments of Present Invention In order to confirm whether or not Compound 1 of embodiments of the present invention has an effect of alleviating skin redness as well as the effect of protecting the skin against UV light (Example 10), a clinical test of a product containing Compound 1 of embodiments of the present invention on the effect of alleviating skin redness was performed through Korea Dermatology Research Institute.

As a specific test method, a product using a white cream as a vehicle and containing Compound 1 of embodiments of the present invention was prepared, and the clinical test was performed on 12 subjects having skin redness for a total of 4 weeks. Left and right cheek sites of the faces of the subjects were randomly assigned as a test sample application site and a control sample application site, and the product containing Compound 1 and the vehicle corresponding to the control sample were self-applied twice a day (in the morning and evening), respectively. After measuring skin redness of the left and right cheek sites of the faces corresponding to the test sites 5 times, respectively, using a chromameter on 2 weeks and 4 weeks, skin redness indices (a-values) were arithmetically expressed. A composition containing Compound 1 of embodiments of the present invention was prepared using ingredients illustrated in the following Table.

| Ingredient | Content of test sample (wt %) | Content of control sample (wt %) |
| --- | --- | --- |
| Compound 1 | 2.0 | — |
| Deionized Water | 73.3 | 75.3 |
| Propanediol | 5.0 | 5.0 |
| Polyglycerin-3 | 5.0 | 5.0 |
| 1,2-hexanediol | 2.0 | 2.0 |
| Xanthan gum | 0.1 | 0.1 |
| Acrylate/C10-30 alkylacrylate cross polymer | 0.3 | 0.3 |
| Glyceryl stearate SE | 3.0 | 3.0 |
| Vegetable oil | 3.0 | 3.0 |
| Dicapryl ether | 3.0 | 3.0 |
| cyclomethicone | 3.0 | 3.0 |
| Arginine | 0.3 | 0.3 |

The results were illustrated in FIG. 13, and as illustrated in FIG. 13, in the control site, skin redness improvement rates after 2 weeks and 4 weeks of the test were −5.34% and −5.15%, respectively, such that the effect was not exhibited. On the contrary, in the test site in which the product containing Compound 1 of embodiments of the present invention was used, the improvement rates were 5.93% and 13.23% after 2 weeks and 4 weeks of the test, respectively. Therefore, it may be appreciated that Compound 1 of embodiments of the present invention has the effect of alleviating skin redness.

The cosmetic composition according to embodiments of the present invention contains the compound inducing adiponectin and autophagy activation according to embodiments of the present invention or the pharmaceutically acceptable salt thereof, such that the cosmetic composition increases expression of adiponectin and proteins associated with the autophagy activity to suppress decomposition of MMP-1 genes increased by sun light, particularly, UV light, thereby making it possible to prevent and treat wrinkles, skin aging, and skin redness due to photo-aging.

Further, the medicinal composition according to embodiments of the present invention contains the compound inducing adiponectin and autophagy activation according to embodiments of the present invention or the pharmaceutically acceptable salt thereof as an active ingredient to decrease expression of inflammatory cytokines, interleukin-6 (IL-6) and IL-8, thereby decreasing skin inflammation caused by light. Therefore, the medicinal composition according to embodiments of the present invention is significantly effective in preventing and treating skin inflammatory diseases caused by light.

What is claimed is:

1. A method of treating skin inflammation, the method comprising:
topically applying a composition to a subject's skin to induce expression of adiponectin in tissues of the skin in need of such treatment, wherein the composition comprises an effective amount of a compound of Chemical Formula 2 or a pharmaceutically acceptable salt thereof:

[Chemical Formula 2]

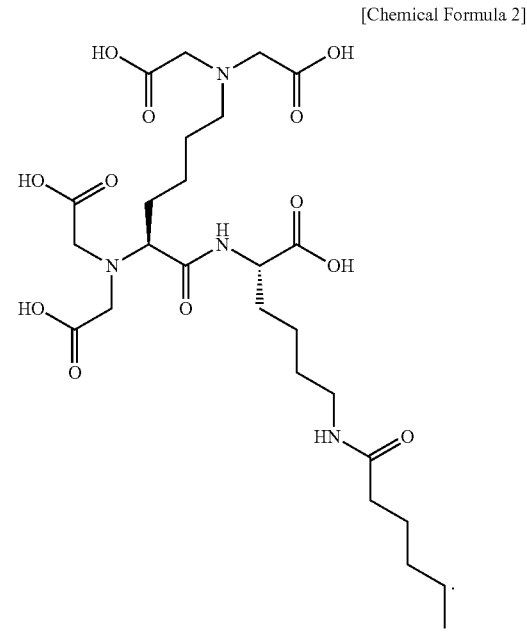 [SMILES: CCCCCC(=O)NCCCC[C@H](NC(=O)[C@H](CCCCN(CC(=O)O)CC(=O)O)N(CC(=O)O)CC(=O)O)C(=O)O]

2. The method of claim 1, wherein applying the composition to the skin that is UV-damaged.

3. The method of claim 1, wherein the composition comprises the compound or the pharmaceutically acceptable salt thereof in an amount of 0.0001 to 10 wt % with reference to the total weight of the composition.

4. The method of claim 1, wherein the composition further comprises at least one selected from the group consisting of a perfume, a colorant, a disinfectant, an anti-oxidant, a preservative, a moisturizer, a stabilizer, an emulsifier, a thickener, a liquid crystal membrane reinforcing agent, a pigment, an excipient, a diluent, inorganic salts, and a synthetic polymer material.

5. The method of claim 1, wherein the composition is in a formulation selected from the group consisting of a suspension, an emulsion, a paste, a gel, a cream, a lotion, a powder, a soap, a surfactant-containing cleansing formulation, an oil, a powder foundation, an emulsion foundation, a wax foundation, and a spray.

* * * * *